(12) United States Patent
Levine

(10) Patent No.: US 9,752,914 B2
(45) Date of Patent: Sep. 5, 2017

(54) MEASURING APPARATUS SYSTEM AND METHOD

(75) Inventor: Noam Levine, Modiin (IL)

(73) Assignee: FIZE RESEARCH LTD, Modin (IL)

( * ) Notice: Subject to any disclaimer, the term of this patent is extended or adjusted under 35 U.S.C. 154(b) by 366 days.

(21) Appl. No.: 12/490,414

(22) Filed: Jun. 24, 2009

(65) Prior Publication Data

US 2009/0314101 A1    Dec. 24, 2009

Related U.S. Application Data

(60) Provisional application No. 61/075,029, filed on Jun. 24, 2008.

(51) Int. Cl.
| | |
|---|---|
| *G01F 1/00* | (2006.01) |
| *G01F 23/02* | (2006.01) |
| *A61F 5/44* | (2006.01) |
| *G01F 1/56* | (2006.01) |
| *G01F 23/26* | (2006.01) |
| *A61M 25/00* | (2006.01) |

(52) U.S. Cl.
CPC ............. *G01F 23/02* (2013.01); *A61F 5/44* (2013.01); *G01F 1/007* (2013.01); *G01F 1/56* (2013.01); *G01F 23/266* (2013.01); *A61M 25/0017* (2013.01)

(58) Field of Classification Search
None
See application file for complete search history.

(56) References Cited

U.S. PATENT DOCUMENTS

| | | | | |
|---|---|---|---|---|
| 4,291,692 | A | * | 9/1981 | Bowman et al. ............... 604/31 |
| 4,343,316 | A | * | 8/1982 | Jespersen ..................... 600/584 |
| 4,481,828 | A | * | 11/1984 | Cheng ........................ 73/861.63 |
| 4,712,567 | A | * | 12/1987 | Gille et al. ..................... 600/584 |
| 5,062,304 | A | * | 11/1991 | Van Buskirk et al. ......... 73/861 |
| 5,137,033 | A | * | 8/1992 | Norton ........................ 128/886 |
| 5,146,788 | A | * | 9/1992 | Raynes ........................... 73/708 |
| 5,769,087 | A | * | 6/1998 | Westphal et al. ............ 600/573 |
| 6,063,043 | A | * | 5/2000 | Meyer et al. ................. 600/586 |
| 2005/0256447 | A1 | * | 11/2005 | Richardson et al. ........... 604/65 |
| 2008/0312556 | A1 | * | 12/2008 | Dijkman ...................... 600/584 |
| 2010/0280445 | A1 | * | 11/2010 | Gelfand et al. ................ 604/66 |

\* cited by examiner

*Primary Examiner* — Robert R Raevis
(74) *Attorney, Agent, or Firm* — Vladimir Sherman; Professional Patent Solutions

(57) ABSTRACT

Disclosed are a method, device and system for determining a flow rate of an excretion stream within an excretion collection assembly. According to some embodiments of the present invention, one of the constituent elements of the collection assembly includes a sensing module which includes an electrical and/or electromechanical component.

20 Claims, 15 Drawing Sheets

MEASURING APPARATUS SYSTEM AND METHOD

FIELD OF THE INVENTION

The present invention relates generally to the field of healthcare. More specifically, the present invention relates to systems, apparatuses, mechanisms, circuits and methods which may be used to determine urine discharge rate and volume of a patient.

BACKGROUND

Note: The terms "Foley catheter", "bladder catheter", "urinary catheter" or simply "catheter" are used interchangeably throughout this document.

For simplicity of the description, the present invention will mainly be explained in connection with urine flow measurement. The same or similar ideas, apparatuses, techniques, circuits and methods can be used or adopted for the measurement of other fluids in general and other body fluids in particular such as blood or intravenous solution.

In many cases during patient treatment it is necessary to collect and determine continuously the accurate amount of discharged urine from the patient's body. This is routinely done for patients during operations, post-operative patients, patients in intensive care units (ICU), as well as those with urologic disorders where, for example, urine output is directly related to renal function. This type of procedure for collecting, measuring and monitoring urine takes on extreme importance because, for example, sudden changes in urine flow, which can occur at any time, can indicate that there is a deteriorating clinical condition in the patient. Changes in urine output have been correlated with changes in cardiac output. The invasive collection of urine and measurement of urine output are typically accomplished by first catheterizing the patient, i.e. a catheter is passed through the urethra of the patient into the bladder. The other end of the catheter is connected to a container or drainage bag through a length of flexible tubing. Typically the bag is supported below the patient from the patient's bed or other support system such as a wheelchair, and urine drains by gravity force from the patient through the flexible tubing and into the collection bag (FIG. 1). In addition to monitoring urine output as a function of time, the reservoir of a collection bag fills to capacity at unpredicted intervals and someone must empty or replace the bag so it can fill once again with urine. Patients can sometimes obstruct the flow of urine into the bag by lying on the drain tube. Further, if there is blood in the urine, blood clots can form that may clog the catheter. In these cases, no urine appears in the bag after an expected time period. Both a filled bag and blocked tube can cause urine backup and a backup could cause deleterious effect on the patient's condition. For all the above and other reasons, monitoring collection bags and accurately and reliably measuring the urine flow is an important part of providing effective patient therapy.

In order to measure the patient's urine discharge, the urine drainage bag typically has measurement graduation marking on the bag's wall. Once in a predetermined amount of time (e.g. one hour), the nurse or doctor visually checks the urine level in the bag according to the marking and records it in a table in the patient's file. When a more accurate urine flow measurement is required, the measurement is done using a measuring device (FIG. 2). The device is placed in between the catheter and flexible tubing that leads the urine from the bladder, and the urinary drainage bag (FIG. 3). One such device (FIG. 2) is a container that has a volume of about 100-300 ml, and is made of transparent material with graduated markings (21) along its height. The container has an inlet on the top that connects to the tubing (24) carrying the urine from the bladder catheter and an outlet (26) with a valve (27) on the bottom of the container connected to the drainage bag. Initially, the valve at the bottom of the container is placed in the closed position and all the urine that flows from the bladder is being collected in the container. Other designs of such a measuring device are connected in other ways to the drainage bag, for example, with a tube connected from the top of the container to the drainage bag. An example of such a device is described in U.S. Pat. No. 3,345,980. Once in a predetermined time interval (e.g. one hour), the nurse or doctor checks the amount of urine that was collected during that period of time according to the urine liquid level in the container and records it in a table in the patient's file. After the urine volume is read, they then pour the urine accumulated in the container to the drainage bag, either by opening the valve on the bottom of the container or by tilting the container and letting the urine flow through the tubing that connects to the drainage bag or in any other way depending on the type of measuring device used. After emptying the measuring container, it is ready for a new measuring cycle of the predetermined amount of time.

SUMMARY OF THE INVENTION

The present invention is a measuring apparatus system and method for measuring body fluid flow rate in general and excretion stream, such as urine flow rate in particular. According to some embodiments of the present invention, there may be an excretion collection assembly that may include a bag, a tube, a catheter, and a measurement probe which may also be referred to as a "measurement unit" or as a "measuring device". According to some other embodiments of the present invention, there may be an excretion collection assembly that may include a bag, a tube, and a catheter. According to some embodiments of the present invention, there may be a sensing module for sensing the fluid flow. According to some embodiments of the present invention, the sensing module may include at least one electrical component and/or at least one electromechanical component. According to some embodiments of the present invention, at least a portion of the sensing module may be integral with a bag of the assembly. According to some embodiments of the present invention, at least a portion of the sensing module may be integral with a catheter of the assembly. According to some embodiments of the present invention, at least a portion of the sensing module may be integral with a tube of the assembly. According to some embodiments of the present invention, at least a portion of the sensing module may be integral with a measurement probe of the assembly. According to some embodiments of the present invention the sensing module may include a nonvolatile memory (NVM). According to some embodiments of the present invention, the nonvolatile memory may store calibration information. According to some embodiments of the present invention the sensing module may include a random access memory (RAM). According to some embodiments of the present invention, the random access memory may store flow measurement data. According to some embodiments of the present invention, the sensing module may include a passive electrical element such as a coil, piezoelectric crystal, motor, solenoid, capacitor, resistor, light emitting diode (LED), laser diode, thermocouple, bimetal and/or a switch. According to some embodiments of the present invention the electrical component that may be included in the sensing module may be an integrated circuit (IC). According to some embodiments of the present invention, the electrical component and/or electromechanical component that may be included in the sensing module may be powered by at least one battery. According to some embodiments of the present invention, the electrical component and/or electromechanical component that may be included in the sensing module may be powered by at least one rechargeable battery. According to some embodiments of the present invention, the electrical component and/or electromechanical component that may be included in the sensing module may be powered by a chemical reaction associated with the excretion. According to some embodiments of the present invention the electrical component and/or electromechanical component that may be included in the sensing module may receive power through an electrical wire that may be connected to an electrical power source. According to some embodiments of the present invention, the electrical component and/or electromechanical component that may be included in the sensing module may be adapted to transmit a signal indicative of excretion flow to an external device. According to some embodiments of the present invention, the electrical component and/or electromechanical component that may be included in the sensing module may be adapted to transmit a signal indicative of excretion flow through an electrical wire to an external device. According to some embodiments of the present invention, the wire may include a connector which may include a non-volatile memory. According to some embodiments of the present invention, the electrical component and/or electromechanical component that may be included in the sensing module may be adapted to transmit a signal indicative of excretion flow to an external device, wirelessly. According to some embodiments of the present invention, the system of the present invention may be discrete. According to some embodiments of the present invention, the system of the present invention may include a calibration parameter. According to some embodiments of the present invention, the calibration parameter may reflect at least one characteristic of the electrical component and/or electromechanical component that may be included in the sensing module. According to some embodiments of the present invention, the calibration parameter may be adjusted during production or sorting of the electrical component and/or electromechanical component. According to some embodiments of the present invention, the calibration parameter may be adjusted during production or sorting of the sensing module.

In hospital settings (e.g. ICU and operation room settings) where patients may be attached to urinary catheters for monitoring urine volume, the conventional measuring device's readings may be manually logged in a tabular format. This method of urine flow measurement may be inaccurate and may not provide real-time information.

The inaccuracy may be a result of several parameters:

1. The reading may only be as accurate as the resolution of the graduating on the measuring container wall.
2. The reading may need to be done in precise time intervals, but in practice the time can vary, and in some cases even up to 50%.
3. The reading intervals may typically be once an hour, this time interval does not let for a continuous flow measurement.
4. The urine discharge from the bladder may have a burst flow nature, this means that the reading accuracy may be limited to the amount of urine in a burst.
5. Urine flowing from the bladder while the measuring container is being drained into the collecting bag may not be measured.
6. Usually the nurse does not lift the tubing in order to drain all the residual urine that may be in the tube to the measuring device before reading the urine quantity. This causes a situation in which the periodical measurements may be performed while in the tubing there may be each time a different amount of residual urine and not in an identical condition in which the tubing may always be empty.
7. If the measuring container is not leveled, the tilt may cause an inaccurate reading.
8. If the measuring container fills to its maximum capacity before being emptied, the collected urine may overflow and may not be measured.

Other disadvantages of the current measuring method may be:

1. Since the measuring device may need to be lower than the patient for the urine to flow by gravity force, it may usually be attached to the bedside at a low place or under the bed. This may make the reading of the urine level not comfortable for the hospital personnel as they may need to bend over in order to accurately see the urine level.
2. At night time when the room is darkened, it may be difficult to read the measurement unless light is turned on which may disturb the patient and his roommates.
3. The measurement may require human intervention and may consume precious time of a nurse who may usually have urgent tasks to deal with.
4. There may be a delay from the time urine was excreted from the bladder until it flows into the measuring container due to accumulation of urine in the tubing. With children, this delay can be very significant as the amount of urine discharged may be significantly less than that of adults.
5. When measuring urine discharge from children, the quantity of urine can be ten times less than that of an adult, therefore the inaccuracies can be very large. For instance, if an adult produces 50 ml and the residual urine in the tubing is 5 ml, the inaccuracy as a result of this factor may be 10%. But if a child produces 5 ml and the residual urine in the tubing is 5 ml, the inaccuracy as a result of this factor may be 100%.
6. If reading the measuring device is delayed for any reason or if there is a high amount of urine discharge, the conventional measuring device may fill to its maximum and overflow, which may cause the amount that overflowed not to be measured.

DETAILED DESCRIPTION

Figure 1:
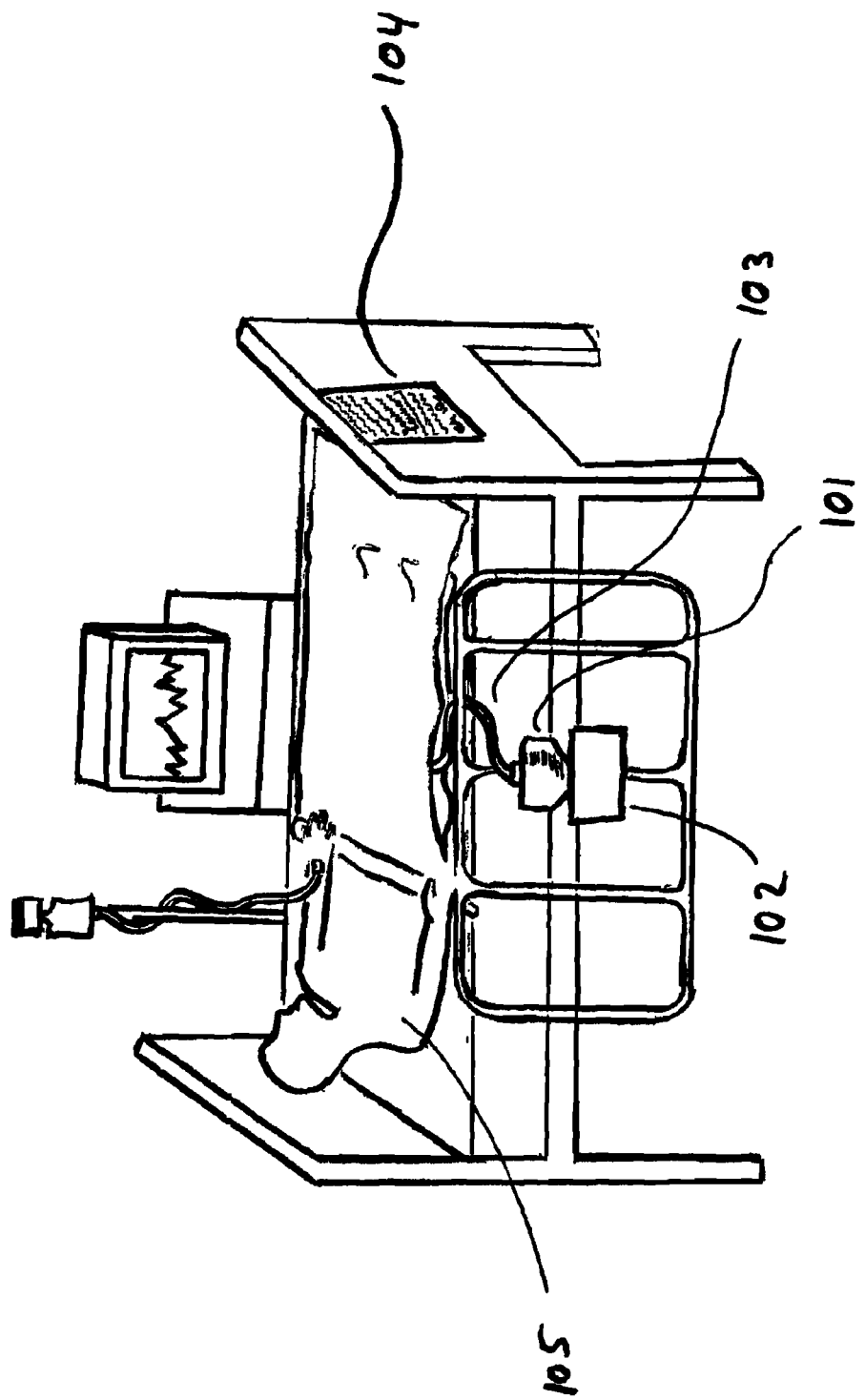
FIG. 1 is a typical setting for measuring urine excretion as currently used in hospitals

Given the problems described in the Background, there may therefore be a need for an apparatus that will overcome these problems.

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention. Unless specifically stated otherwise, as apparent from the following discussions, it is appreciated that throughout the specification discussions utilizing terms such as "processing", "computing", "calculating", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices. Embodiments of the present invention may include apparatuses for performing the operations herein. Such apparatus may be specially constructed for the desired purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, DVDs, magnetic-optical disks, read-only memories (ROMs), random access memories (RAMs) electrically programmable read-only memories (EPROMs), electrically erasable and programmable read only memories (EEPROMs), FLASH memories, magnetic or optical cards, or any other type of media suitable for storing electronic instructions, and capable of being coupled to a computer system bus. The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

The detailed description set forth below in connection with the drawings is intended merely as a description of the presently preferred embodiments of the invention, and is not intended to represent the only form in which the present invention may be constructed or utilized. The description sets forth the ideas, designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

In order to measure urine or liquid flow, a sensing element (sensor) for accurately sensing the flow rate may be provided. Numerous ways can be used for implementing the sensor, these ways can be grouped into several families according to their operating principle.

Some embodiments of the present invention may make use of a family of variable area type of devices. The operating principle is of having a tapered conduit with a variable area along its longitudinal axis, the conduit may have a measuring element in it which can be a ball, a disk, a cone or any other element that obstructs the flow. The measuring element may be forced towards the narrow end of the conduit by a spring or magnet, or electromagnet or gravity or by any other means. The fluid may flow into the conduit from the narrow end and may come out of the conduit from the wide end. The fluid, as it flows, may push the measuring element away from the narrow end and towards the wide end of the conduit, the amount of movement of the measuring element may be proportional to the flow rate, this movement can be visually or electrically measured. In some other implementations of a variable area device the measuring element may be forced to stay in the same location in the conduit, the amount of force applied on the measuring element may be proportional to the fluid flow rate, usually this force may be applied electrically, by, for example, an electromagnet, and the electrical current applied may indicate the flow rate.

Other embodiments of the present invention may make use of a family of droplet count type of devices. These devices are commonly used in intravenous administration sets. The flowing liquid may be collected in a drip chamber to form droplets, the droplets may then be counted in order to determine the drop rate and hence the flow rate. There may be a variety of ways in which the droplets may be counted including, optical—in which the drop may obstruct a light beam; capacitive—in which the drop may fall between the plates of a two plate capacitor and change the capacitance of that capacitor; conductive—in which the drop in its fall may impact on electrical probes and may cause an electrical short-circuit; pressure—in which the failing drop may impinge on a pressure transducer; thermal—in which the drop may impinge on a heated element and may cause it to cool. In more advanced droplet counters, the drop size or volume can also be measured in order to provide a more accurate measurement of the flow rate. There may be a variety of ways the drop volume can be measured, among those are, optical—in which the time it takes the drop to fall across a light beam may be measured or the drop image size on an image sensor may be measured; capacitive—in which the amount of capacitance change of a two plate capacitor may be measured to determine the drop volume failing in between the two plates; pressure—in which the amount of pressure change the impinging failing drop on a pressure transducer causes, may be measured to determine the drop volume; thermal—in which the amount of energy needed to be applied to a heating element in order to keep it in a constant temperature may be measured to determine the amount of heat removed by the impinging drop on that heating element, which may be proportional to the drop volume; resistive—in which the drop may flow on a resistor or on two parallel resistors and may create an electrical contact between them, the resistance may determine the drop size.

Other embodiments of the present invention may make use of a family of rotary piston type devices. The operating principle may be of having a piston rotating within a chamber of known volume as the fluid passes through the chamber, the number of piston rotations may be counted to determine the flow rate.

Other embodiments of the present invention may make use of a family of pressure type of devices. The operating principle may be of having two pressure sensors along a conduit with some means for constricting the flow within the conduit in a point which may be in between the two pressure sensors, the pressure difference between the two sensors may determine the flow rate.

Other embodiments of the present invention may make use of a family of magnetic type of devices. The operating principle may be of having a magnetic field applied to a metering conduit which may result in a potential difference proportional to the flow velocity perpendicular to the flux lines, the magnetic flow meter may require a conducting fluid.

Other embodiments of the present invention may make use of a family of travel time type of devices. The operating principle may be of having a marker inserted into the fluid flow and the travel time of that marker along a known length of a conduit may be measured to determine the fluid flow rate. There may be a variety of markers that can be used, among them are: heat—a heating element may be placed in one point along the conduit and a temperature sensor may be placed in a second point downstream of the heating element, the heating element may receive electrical pulses that may create heat markers in the flowing fluid and the temperature sensor may sense these markers. Other markers may include injecting ions, air bubbles or particles.

Other embodiments of the present invention may make use of a family of heater type of devices. The operating principle may be of having a resistive heating element placed in the flow, the heating element may be heated by an electrical current and the flow of fluid may tend to cool it. Since there may be a relationship between the temperature and the electrical resistance of the heating element, the flow rate can be determined by one of three ways, the required current for keeping the heating element in a constant temperature may be measured, or the current may be measured while applying a constant voltage on the heating element, or the voltage across the heating element may be measured while applying a constant current through it.

Other embodiments of the present invention may make use of a family of ultrasonic type of devices. The operating principle may be of having an ultrasonic wave that may be transmitted in the direction or opposite the direction of the fluid stream, the propagation speed of the wave may be a function of the fluid flow rate.

Other embodiments of the present invention may make use of a group of families for measuring liquid flow which may be based on measuring the volume of the liquid as a function of time, the change in volume divided by the time of that change may determine the flow rate. The fluid may typically be collected in a container for volume measurement, when the container fills up it may be automatically or manually emptied for successive measurements to take place.

One family of volume measurement devices may be the weight type of devices. The container may be continuously weighed to determine the volume and fill rate.

Other families of volume measurement devices may be the capacitive type of devices. The container may have a plate capacitor immersed in it from top to bottom, the liquid may fill the gap between the plates and a change in the liquid level may change the capacitance which can then be measured.

Other families of volume measurement devices may be the resistive type of devices. The container may have a resistor or pair of resistors immersed in it from top to bottom, a change in the liquid level may change the resistance of the resistor(s) which can then be measured to determine the liquid level.

Other families of volume measurement devices may be the ultrasonic type of devices. An ultrasonic transducer may be placed at the bottom or top of the container, the transducer may produce an ultrasonic wave that may progress and may hit the fluid surface and may return back to the transducer, the round trip time may be measured to determine the fluid level.

Other families of volume measurement devices may be the electrode type of devices. The container may have electrodes that extend along the height of the container. The accumulation of liquid in the container may perform an electrical contact between the electrodes, the number of electrodes that the liquid contacts may determine the liquid volume.

The abovementioned families, is not intended to be a complete list of the methods and apparatuses for sensing fluid flow rates, several other families for sensing fluid flow rates can be used or thought of, and the above mentioned were brought just as an example. Similarly, there may be many different implementation ways in each family, and in the places where one or several such ways were mentioned, it was done by way of example only and not with the intention of presenting a complete list of ways.

The present invention is not limited to a particular type of sensor and any type of sensor known today or to be devised in the future can be used for implementing the measuring device of the present invention.

According to some embodiments of the present invention, there may be a measuring device which may determine liquid, such as urine flow rate, and transmit a signal indicative of the flow to an external device. According to some embodiments of the present invention, there may be an excretion collection assembly that may include a catheter, a tube, a measuring device, and a bag. According to some embodiments of the present invention, the measuring device may be a sensing module, at least a portion of which may be integral with a bag or a tube or a catheter of the assembly. According to some other embodiments of the present invention the measuring device may be a measurement probe. The term "measuring device" in the specification of the present invention may refer to the sensing module and/or to the measurement probe.

In order to accurately measure the urine flow, the tube that may connect the bladder catheter to the measuring device may need to be kept full with urine at all time so that any amount of urine entering the tube on one end will cause the exact same amount of urine to come out at the other end and be measured. In order to achieve that, the internal diameter of the tube may need to be small enough so that it may not let air bubbles enter the tube, if air is able to enter the tube the urine that enters the tube from the catheter may not always cause the exact same amount of urine to exit at the other end and be accurately measured, or urine can spill out of the tube into the measuring device and be mistakenly measured while no urine or less urine enters the tube from the catheter. Also, if someone moves or raises the tube, some amount of urine may spill from the tube into the measuring device and be mistakenly measured, while later, urine that will flow from the catheter may be accumulated in the tube and may not be measured for a while. Therefore, by using a tube with a diameter of less than 8 mm the surface tension of the urine may not let the urine pour out as well as also not letting air go in. Another possible construction of the tube may be to have a wide diameter tube with a small diameter end connecting to the measuring device (FIG. 4), this construction of the tube may have the same benefits of not letting air in as well as the benefit of greater resistance to bending which may cause occlusion of the tube and may stop the flow of the urine.

Other constructions of the tube which may achieve the same effect of allowing out only the exact amount of liquid going in may include: Having a wide tube that may connect to a narrow inlet in the measuring device (FIG. 5) or having a tube with varying diameter (FIG. 6*a* and FIG. 6*b*).

The tube can be an integral part of the measuring device where it may be attached to the measuring device during manufacturing, or it can be a separate part that may be connected to the measuring device by the nurse or doctor. The tube can alternatively or additionally be an integral part of the catheter where it may be attached to the catheter during manufacturing.

When a catheter is inserted into the bladder and/or a new tube is connected to the bladder catheter and/or to the measuring device it may first need to fill up with urine until the urine reaches the measuring device and is measured. This time period can be significant, for example, a tube with a 10 mm diameter and a 1 meter length contains an amount of 79 ml. If the urine excretion is at a rate of 30 ml/h then it may take over two and a half hours from the time the tube is connected until measuring may start. In order to minimize the delay from the time the tube is connected to the catheter and/or to the measuring device, or from the time the catheter is inserted to the bladder until the urine measuring starts due to the time it takes the tube to fill up with urine, the tube can be filled with some liquid such as water or saline. Filling up the tube with liquid can be done by the nurse or doctor before or after connecting the tube, or the tube can be pre-filled, for example, during manufacturing, and the nurse or doctor may connect an already filled tube to the measuring device and/or the bladder catheter.

According to some embodiments of the present invention, the measuring device may contain the urine flow path, the urine flow sensing element, the measuring control electronics circuitry, optional individual device calibration data, optional memory for storing the measurements, and the electronic circuitry for transmitting the measurements, integrated as one system (FIG. 7) that may be packaged together in the same sensing module. According to some embodiments of the present invention, the entire, or a portion of the sensing module can be integral with the tube. According to some other embodiments of the present invention, the entire, or a portion of the sensing module can be integral with the urine collection bag. According to some other embodiments of the present invention, the entire, or a portion of the sensing module can be integral with the catheter. According to some other embodiments of the present invention, the entire, or a portion of the sensing module can be integral with a measurement probe connected in between the urine collection bag and the catheter, whether directly connected or indirectly with some tubing in between.

Since the device of the present invention may include the urine flow path that may be connected to the tube that may be connected to the catheter that may be connected to the patient's bladder, the device may either be washable and sterilize-able, or disposable.

In the case where the device is disposable, either when it is integrated as part of the urine collection bag, or as part of the tube, or as part of the catheter, or as part of a measurement probe and discarded as part of the discard of the bag or tube or catheter or measurement probe, or if it is a separate disposable device, the system cost may need to be very low in order to enable it to be practically disposable. This can be achieved by having part or all the electronic circuits and optionally also the flow sensing element or part of it and optionally also the calibration data, and optionally also the measurements memory, integrated into one or more integrated circuit (IC).

The most cost effective solution may be to have part or all the electronic circuits and part or the entire flow sensing element, and part or all the calibration data if it exists, and part or all of the optional measurements memory, integrated into a single integrated circuit.

By having the entire device integrated into one module, either a fully disposable or sterilize-able discrete measuring system, it may be possible to satisfy the objectives of:

1. Accuracy—By having the whole system integrated in one device the measurement may be more exact due to the following reasons.
   There may not be any errors occurring from alignment between a fixed measuring instrument and a disposable or sterilize-able device connected to it.
   There may be greater accuracy because of the great proximity between the urine and the sensing element, this may not be achieved with a two element device.
   The electrical noise level may be very low in a unified discrete system which may lead to a higher SNR (Signal to Noise Ratio) and therefore to higher measurement accuracy.
   A discrete system may enable the construction of much more sensitive and precise sensors than a two element system.
2. Resolution—By having a discrete system greater measuring resolutions can be achieved due to the ability to design more accurate sensors.
3. Continuous reading—A discrete system can perform measurement on very small liquid volume and therefore can provide frequent readings.
4. Delay—Due to the small urine volume that may be required for performing an exact measurement, the time it takes for that volume to flow past the sensor may be relatively short and therefore the reading delay may be relatively small.
5. No fixed part attached to bed—Since the entire system may be disposable or sterilize-able, there may be no fixed part.
6. No sensitivity to shaking—A sensor that requires very small amounts of liquid for measuring the flow may not be influenced by shaking.
7. Handling—A system that may be integrated into the existing equipment (urine bag or tube or catheter or measurement probe) can be used almost in the same way as it is being used today. No special new parts or connections involving the urine may be needed.

8. Cleanness—If the system is disposable, there would be no need to wash, clean and sterilize it before use. The system may be sterilized during manufacturing in the same way as other disposable medical devices.

In order to satisfy the objective of enabling easy and comfortable reading at an eye-level height without need for bending over or turning a light on, the display may be a separate unit. The measuring device can communicate the measured values to the display via electrical cable or optical fiber or wirelessly.

Figure 9:
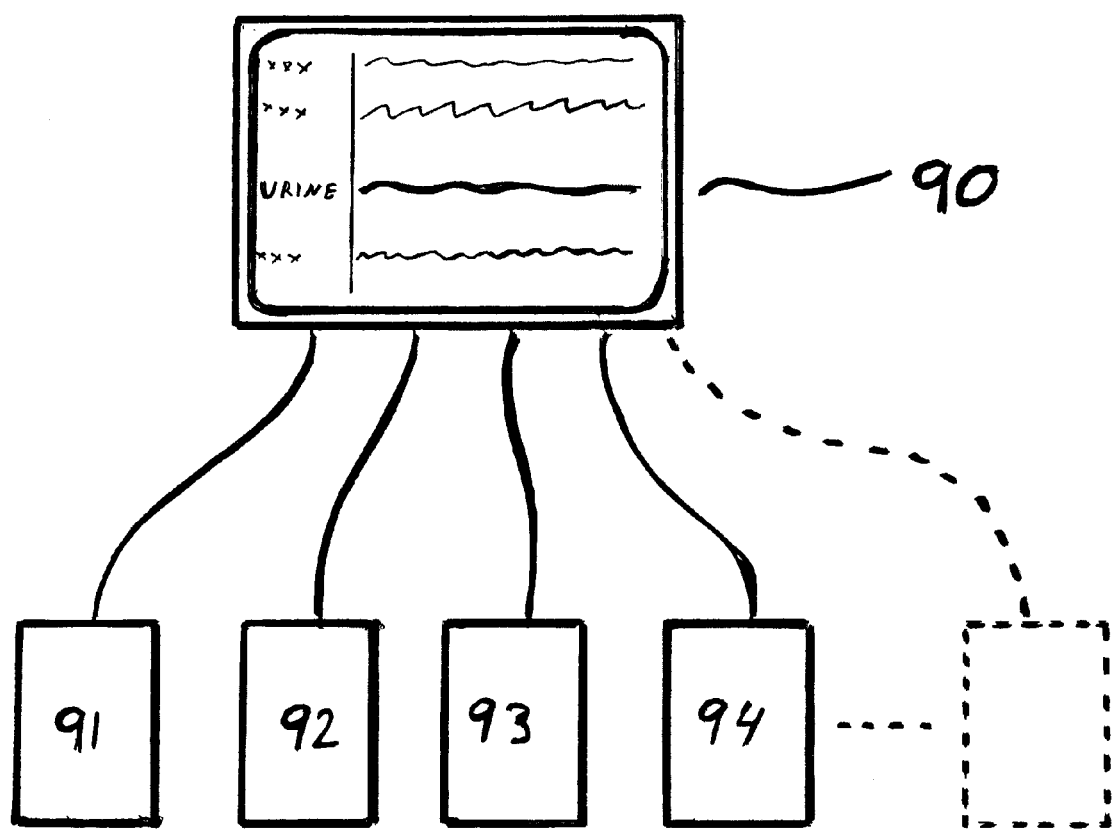
FIG. 9 shows the connection of the measuring device of the present invention to a vital sign monitor
Figure 10:
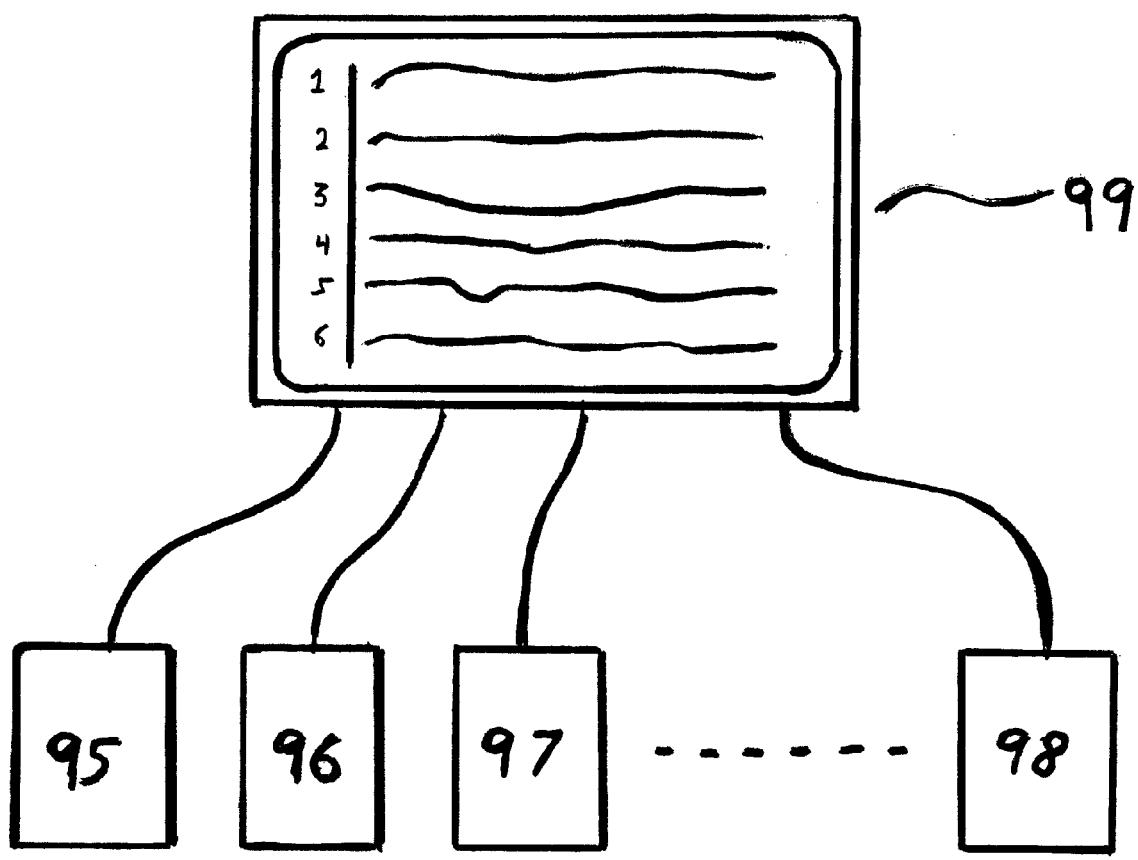
FIG. 10 shows the connection of several measuring devices of the present invention to a central monitor

The display unit can be a dedicated display for displaying only urine flow (FIG. 8), or it can be a standard vital signs monitor that is commonly used in hospitals placed near the patient's bed (FIG. 9), or it can be a centralized monitor, either dedicated for urine or standard vital signs, located in the nurses' station (FIG. 10).

The measuring device may need to be powered by electrical power in order for it to operate. According to some embodiments of the present invention, the device can be powered by one or more of several alternatives.

1. The device may be powered by a battery. If the measuring device is disposable, the battery can either be disposable and part of the disposable device, or, the battery can be attached or inserted to the measuring device before use and detached after the use before the discard of the measuring device, in this case the battery can be rechargeable or not rechargeable. If the measuring device is reusable, the battery may be attached or inserted to the measuring device before use and detached after the use before cleaning and sterilizing the measuring device, in this case the battery can be rechargeable or not rechargeable.
2. The device may be powered by electricity generated from a chemical reaction with the urine.
3. The device may be powered by electricity generated from light.
4. The device may be powered by an electrical cord connected to it from a power source, the power source may be part of the display unit or part of a receiving device or a battery or any other power source.
5. The device may be powered by a magnetic field.

Figure 12:
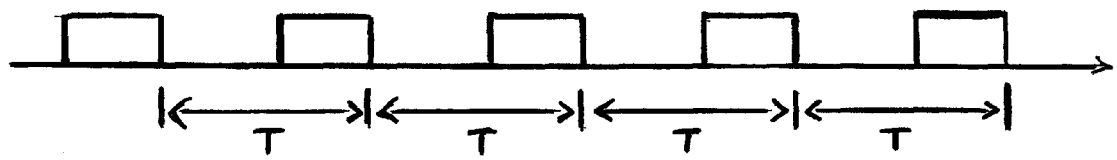
FIG. 12 shows data packets transmitted by a transmitter
Figure 13:
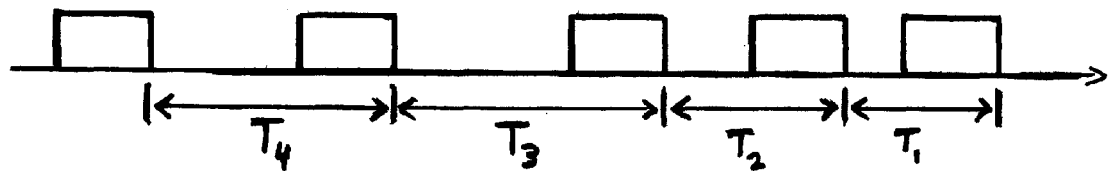
FIG. 13 shows data packets received by a receiver FIG. 14, 15 show data packet rate estimation
Figure 14:
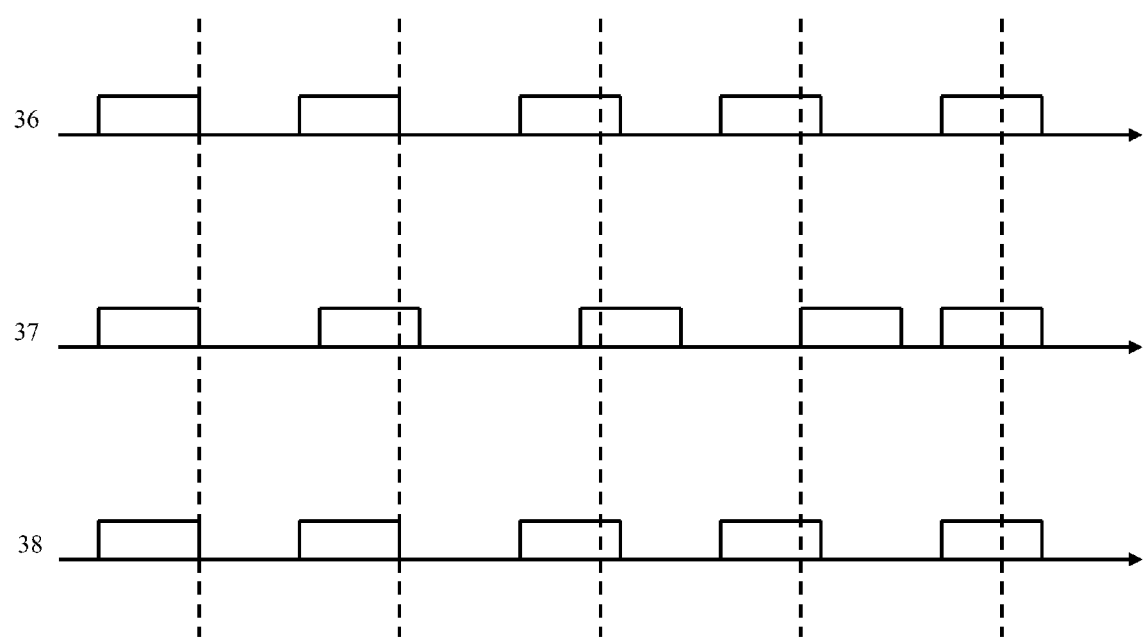
Figure 15:
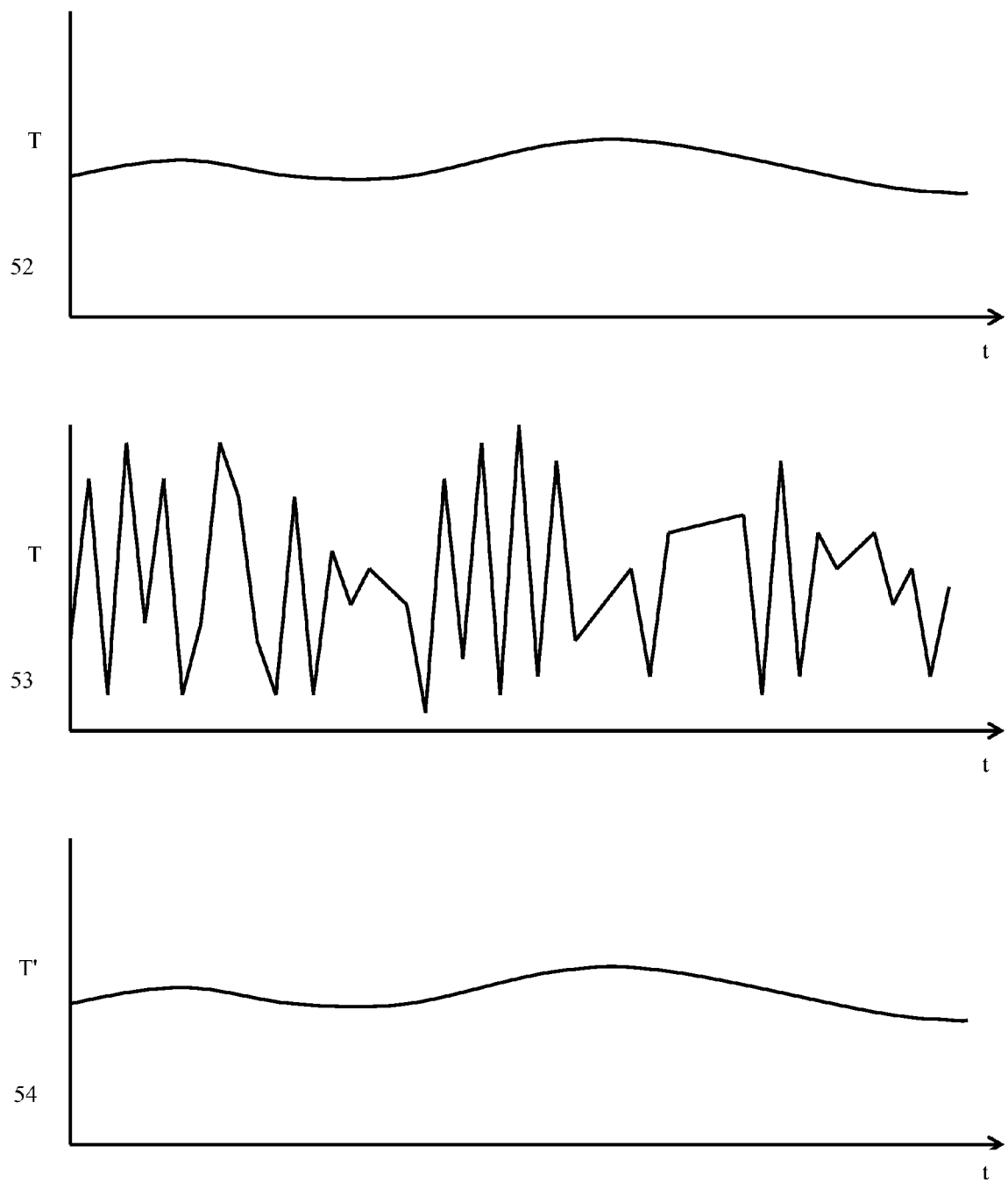

The urine flow of interest may be the flow of urine through the ureters and into the bladder, this may determine the rate of urine produced by the kidneys. The urine flowing out of the bladder through the catheter may have a somewhat burst nature and may not flow in a steady rate. There may be several reasons for these bursts and unsteady flow rate, there may be a brief peristaltic motion 1 to 4 times per minute that affects the pressure on the bladder, in addition there may be movements of the patient that effect the pressure imposed on the bladder, and there may be movements of the catheter and tubing during patient treatment, and movement of the bed by the hospital staff and/or the patient's relatives. All these as well as other reasons may be responsible for the fact that the instantaneous flow of urine out of the bladder may not be exactly identical to the instantaneous urine flow into the bladder. On the other hand, since no urine disappears or accumulates in the bladder, in the long run the average urine flow into the bladder may be equal to the average urine flow out of the bladder. It may be possible to estimate the urine flow in the ureters into the bladder from measuring the urine flow out of the bladder. There are many known ways, algorithms, methods and circuits in the data communication and telecommunication field for recovering an original signal after it passed through a transmission line which added noise or jitter and wander to the original signal. The concepts and notions in the data communication and telecommunication field will now be briefly explained. One particular case will be discussed as an example. Information data may be transmitted from a transmitter (43) to a receiver (45) over a network (44) (FIG. 11), usually the data may be transmitted in what is called packets or cells, in this example these packets or cells are of equal size, and the packets or cells are transmitted at equal intervals of time so that after an amount of time (T) past since the last packet or cell was transmitted a new packet or cell will be transmitted in a way that the time interval between the start of transmission of each packet or cell and the start of transmission of the consecutive packet or cell is (T) (FIG. 12), the rate that the packets or cells are transmitted is 1/T. The transmitted packets or cells travel through the network and the network may add jitter and/or wander to the packets or cells so that the packets or cells received at the receiver may no longer be spaced apart from each other by an amount of time (T) (FIG. 13). Therefore, the receiver may have a mechanism which may estimate the original time interval (T) from the varying intervals (T1, T2, T3, T4, . . . ) between the received packets and may output the packets or cells at the estimated intervals (T'). The estimation mechanism may need to continuously follow any changes in the time interval (T) so that any increase or decrease of (T) on the transmitter side will result in the same increase or decrease in the rate that the receiver outputs the packets or cells (FIG. 14 and FIG. 15). An example of such apparatus can be seen in U.S. Pat. No. 5,396,492.

In an analogous way, the urine flow rate into the bladder may be analogous to the transmitted packet or cell rate, the bladder and the catheter and the tube may be analogous to the network, and the receiver may be analogous to the urine measuring device. Therefore, in an analogous way, the measuring device can estimate the urine flow into the bladder, from observing the urine flow out of the bladder. This estimation can be done by mathematical computation in the measuring device, the computing circuitry can be integrated in the same integrated circuit as other circuits of the measuring device or it can be separate, or the rate estimation can be done outside of the measuring device as in a receiving device or in the display unit.

There may be cases when the patient may be transferred from one location to another like from the ICU to an operation room or to an x-ray or CT examination. In these cases, if the display unit is not connected to the bed, but for instance, is fixed to the wall, the measuring device may need to be disconnected from the display unit and connected to another display unit at the second location. When the measuring device is connected to the second display unit in the second location, all the measurement data that may have been collected while in the first location may be lost and there may not be any information regarding how much urine was excreted during that time as well as the excretion rate. In addition, there may not be any information regarding the amount of urine excreted while the patient was in transit. Also, when the patient is returned to the first location, all information since he left that first location and until he was returned back to that first location may be lost. In order not to lose any information collected, and in order to be able to keep measuring while not being connected to a display unit, there may be according to some embodiments of the present invention an option to have a memory in the measuring device which may store the measurements. This optional memory can be integrated in the same integrated circuit (IC) with other electronic circuits of the measuring device for cost saving. When the measuring device is reconnected to the second display unit, the measuring device may transfer the stored measurements to the display unit for display or for retrieving past excretion information.

The amount of urine excreted may be in the range of less than 5 ml/hr by infants to over 100 ml/hr for adults. Measuring low flow rates like this may require very fine mechanics. Manufacturing such small mechanics to a high degree of accuracy may be very costly. Therefore, in order for the measuring device to be accurate, while keeping manufacturing costs low, the device may be calibrated. Typically this calibration may be done during manufacturing or sorting, and calibration information may be extracted during the calibration process. In addition, many of the flow sensing techniques described above as well as other techniques, involve analog circuitry which may need to be calibrated due to variations in the electrical component values. In addition, in many cases the sensor, which may be for example a resistive or capacitive sensor, may need calibration. The calibration can be done in the factory for each measuring device. During the calibration process, calibration data may be collected. According to some embodiments of the present invention the calibration data may be stored in a non volatile memory (NVM) in the device. The NVM can be integrated in the same integrated circuit with other electronic circuits of the measuring device. It should be noted that the need for calibration may depend on the type and construction of the measuring device, the type of sensor used, and is not always required.

FIG. 1 presents an example of a conventional ICU setting in which a tube (103) is connected to a catheter (not shown) which is inserted through the ureter to the patient's (105) bladder. The tube leads the urine to a measuring device (101) which collects the urine. The urine quantity in the measuring device may then periodically (e.g. each hour) be read and recorded in the patient's file (104) and then emptied into the drainage bag (102). The empty measuring device may then start a new measuring cycle.

Figure 2:
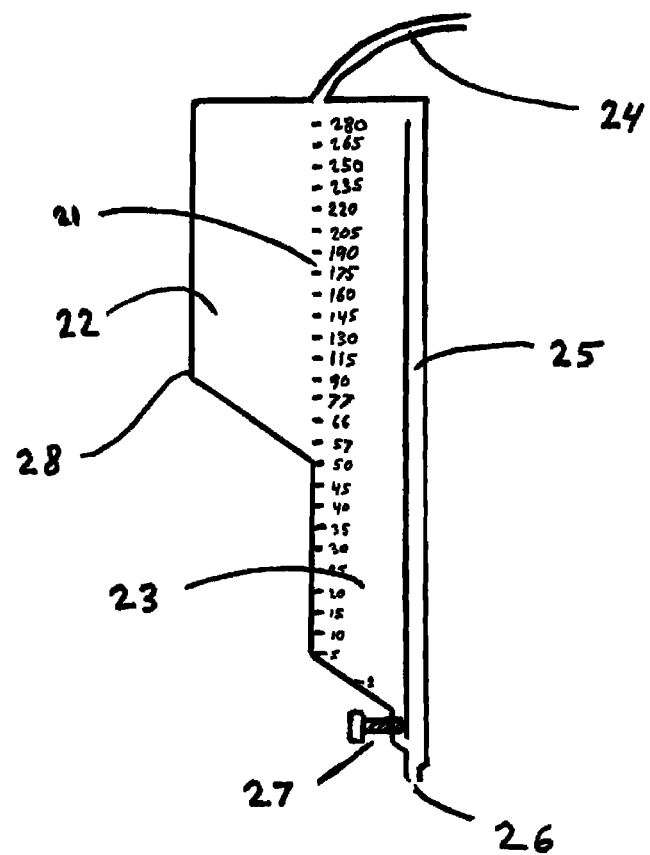
FIG. 2 is a typical urine measuring device which is currently used in hospitals FIG. 3 describes the way the currently used measuring device is connected FIG. 4, 6a, 6b are designs of a tube for accurately measuring the urine flow

FIG. 2 shows an example of a conventional measuring device which is commonly used in hospitals, for example, in ICUs and operation rooms. This type of measuring device may require the attention of a nurse which each hour or some other predefined time interval may read the amount of urine that accumulated in the device and may then empty it into the urine collecting bag to start a new measuring cycle. The conventional measuring device (28) may be made of a transparent material so that the urine level accumulating in the device can be visualized through the device's wall. The device may fill up with urine entering from a tube (24) that may be connected to the top of the device, the urine may fill up the device from the bottom upwards, and the urine quantity can be read by watching the urine level according to the graduated markings (21) that may be on the device's wall. The crosscut of the lower part (23) of the device may be smaller then that of the higher part (22) in order to have a finer resolution when the urine quantity is small. After the urine quantity is read, the valve (27) may then be opened to empty the measuring device into the urine drainage bag (34 in FIG. 3) connected to the device's outlet (26). After the device is empty, the valve (27) may then be closed and a new measuring cycle may start again. In the case that the nurse did not come to read the device on time, or in the case when the urine excretion was abnormally high and the conventional measuring device is filled to the top, any additional urine entering the device may overflow through the bypass channel (25) directly to the urine drainage bag, this may be done in order to prevent backpressure on the bladder.

Figure 3:
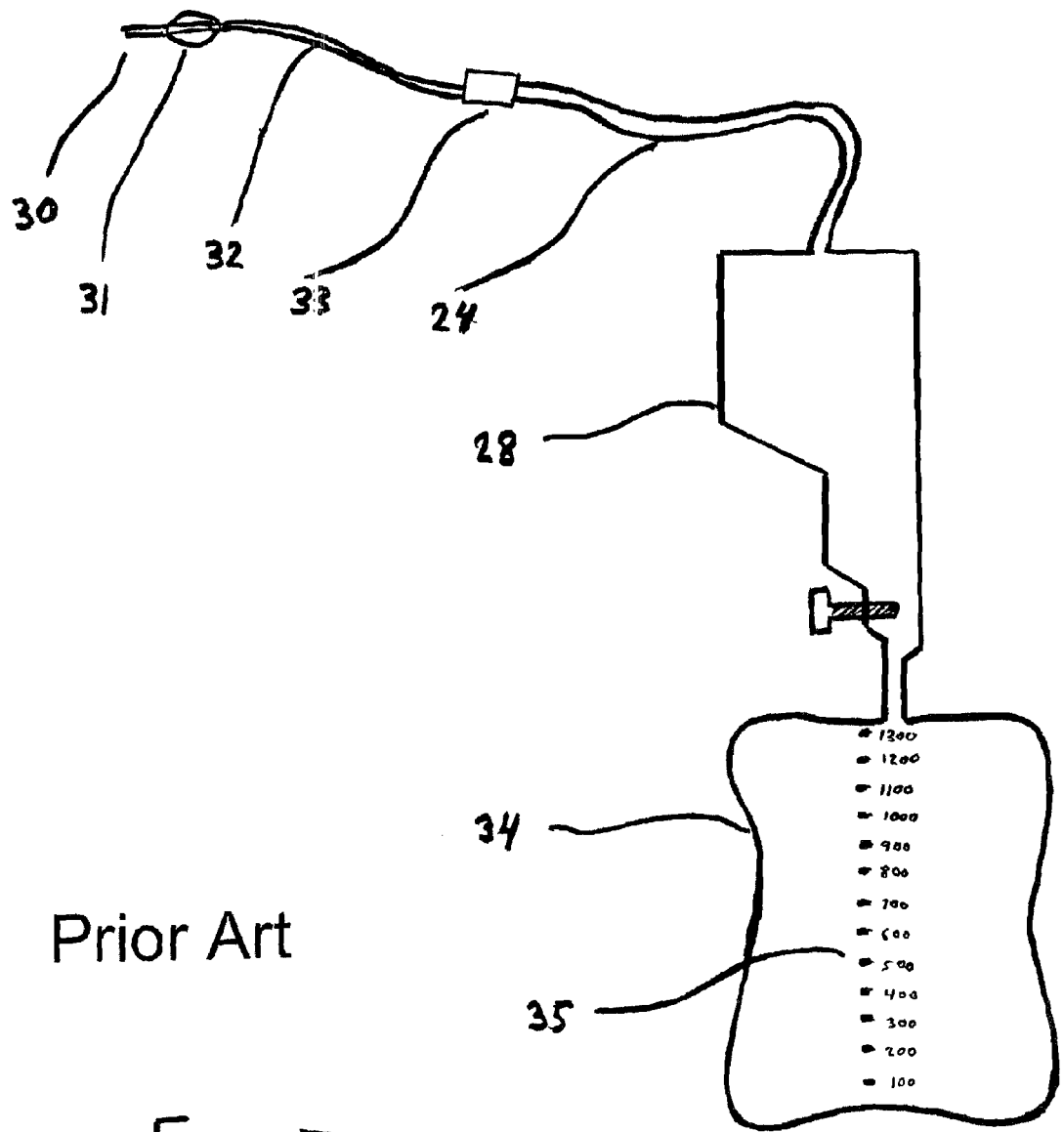

FIG. 3 describes an example of an excretion collection assembly showing how the measuring device (28) may be connected in order to measure urine excretion. The tip (30) of the Foley catheter (32) may be inserted through the urethra and into the bladder, then, the balloon (31) may be inflated using sterile water in order to retain the catheter in the bladder. The inlet of the measuring device (28) may be connected to the Foley catheter (32) using tube (24) which may be connected to the catheter by means of connector (33). The outlet of the measuring device may be connected to the drainage bag (34). The drainage bag may have graduation markings (35) on it so that the amount of urine collected in the bag can be roughly determined.

Figure 4:
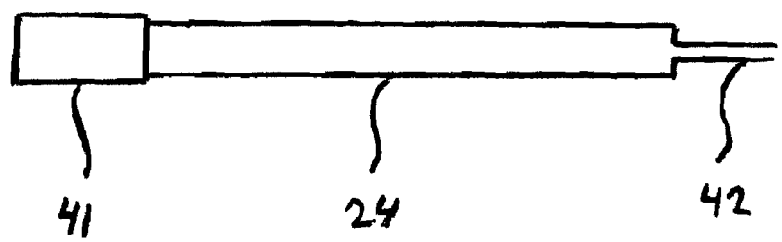

When urine enters a tube with a wide diameter of over 10 mm, the urine can come out of the other end by gravity force and there may not be a direct relation between the flow rate into the tube and the flow coming out of the tube. FIG. 4 shows an example of a design of a tube that may allow the urine to come out of the tube only at the same rate it enters the tube. According to this design, tube (24) may connect to the bladder catheter by means of connector (41), the tube (24) can be of any width. The outlet of the tube (42) may have a width of less then 8 mm, in this way the urine in the tube can not spill out of the tube because air may not be able to enter the tube due to the surface tension of the urine.

Figure 5:
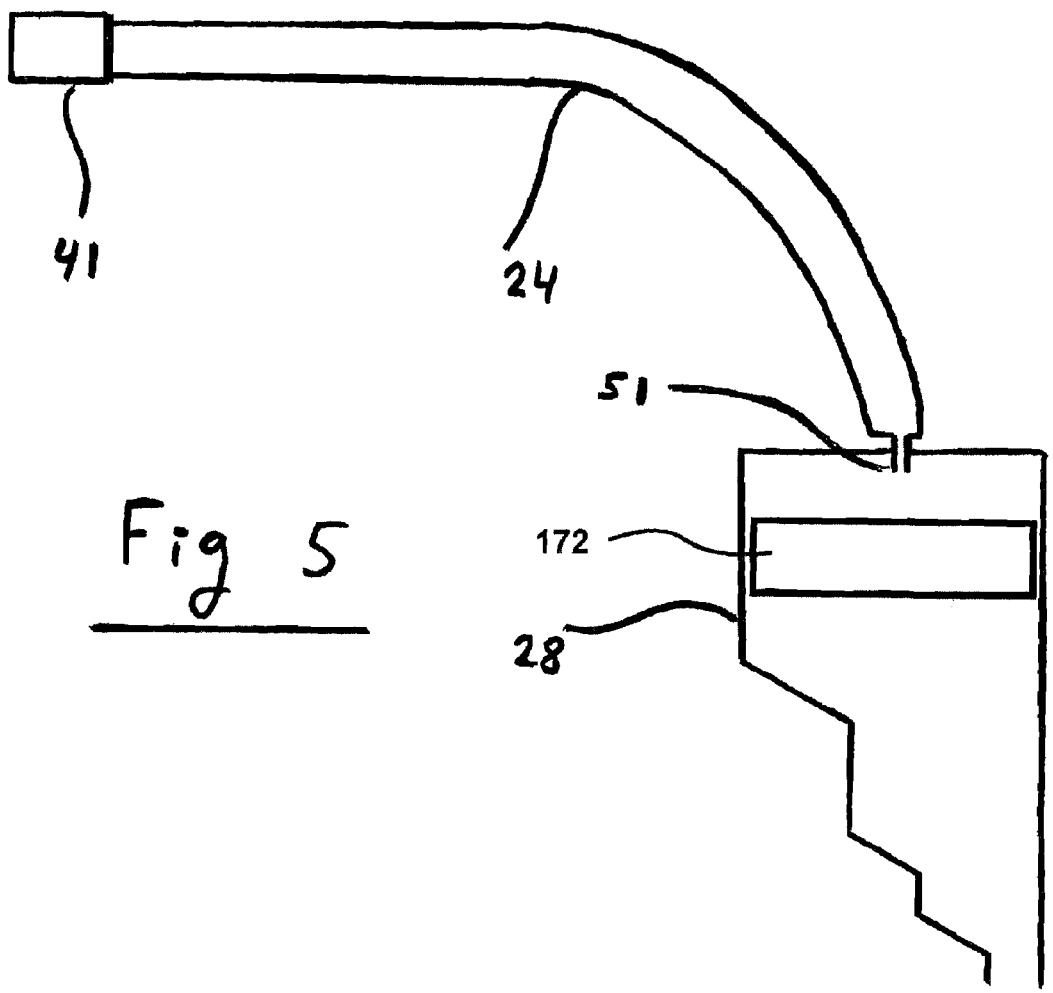
FIG. 5 is a design of the measuring device inlet for accurately measuring the urine flow
Figure 6A:
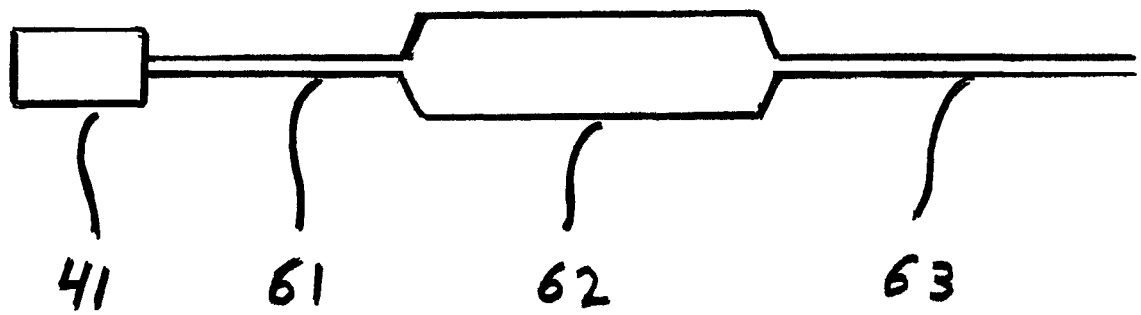
Figure 6B:
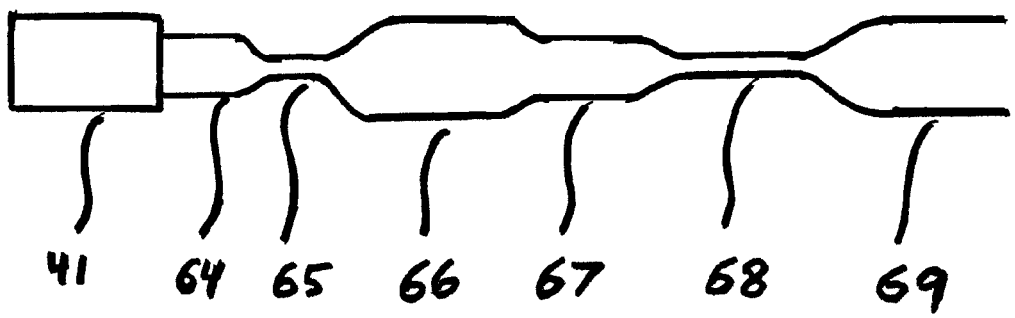

FIG. 5 shows another way of achieving the goal of not letting air enter the tube and causing urine to spill out, by having a tube (24) of any width that may be connected to the urinary catheter by means of connector (41) and may be connected to the measuring device (28) via an inlet (51) of less then 8 mm.

FIGS. 6a and 6b are other designs for achieving the same goal. In these two designs the width of the tube can vary, diameters 61-69 can be of any and different widths. If the tube is connected to the measuring device via a narrow inlet as in 51 then the end of the tube can be wide as in 69, otherwise the end of the tube may be less then 8 mm as in 63.

Figure 7:
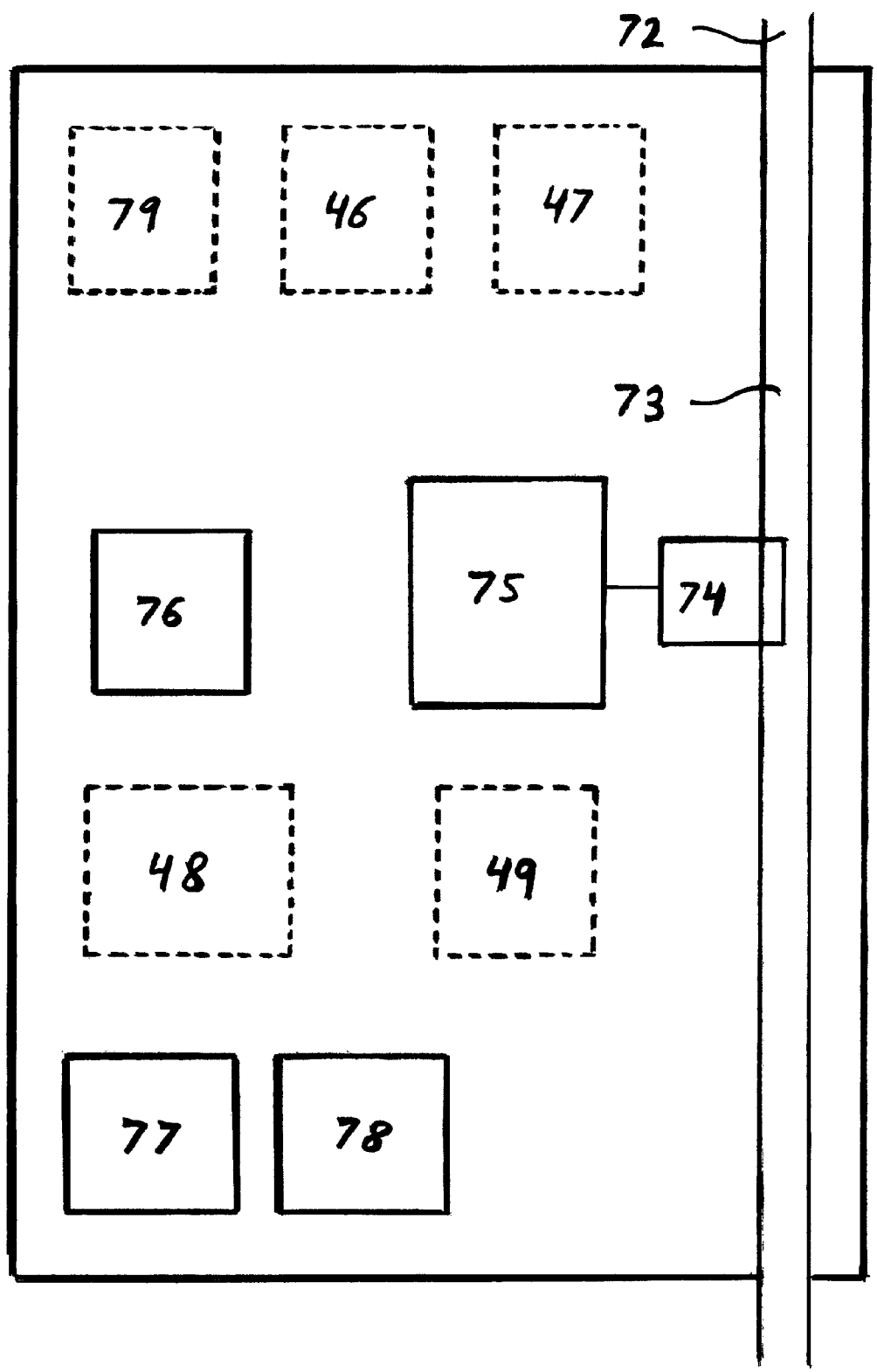
FIG. 7 is a schematic diagram of different embodiments of the measuring device of the present invention

Going now to FIG. 7, a schematic description of the measuring device according to some embodiments of the present invention is shown. The liquid to be measured may enter the measuring device at inlet (72) and may pass through the liquid path (73) to the outlet of the measuring device (71). A sensing element (74) may sense the flow rate. The sensing element can be of any type, including any one of the types discussed above or any other type known today or to be devised in the future. An electronic circuitry (75) may be connected to the sensing element in order to produce a signal that may represent or be indicative of the flow. This circuitry may include analog and/or digital components that may operate together with the sensing element and/or control the sensing element. For example, if a rotor meter is used as the sensing element (74), the number of turns of the rotor may need to be counted, this can be done for example optically, in this case the electronic circuit (75) may include a light emitting element such as an LED, a light detecting element as a phototransistor, and the associated analog circuitry for signal conditioning of the phototransistor signal as well as analog circuitry for adjusting the intensity of the LED. The electronic circuitry (75) may also include some digital circuits for counting the number of turns of the rotor. It should be noted that circuitry (75) may depend on the type of sensing element (74) used. Since the flow of liquid may be measured at one point (e.g. outside of the patient's body), there may be a need to estimate the flow rate as it was in another point upstream (e.g. in the ureters), for this purpose there may be optional circuitry (49) for estimating the flow at the other point. The flow estimation can alternatively be done by a microprocessor or microcontroller or DSP (48) that may optionally be in the measuring device. The measurements may then be communicated to an external receiving device by communication circuitry (78), the communication link (not shown) can be wired, optical, or wireless. The measuring device may be powered by a power source (77) which can be a battery, a photovoltaic cell, a chemical reaction element, a coil or other mean for receiving electromagnetic energy, a wire connected to a power source or any other powering means. The measuring device's operation may be controlled by circuitry (76) which may be optional in a simple design of the measuring device. The measuring device may optionally include a microprocessor or microcontroller or DSP (48) that can perform a variety of tasks like generally controlling the measuring device, lighting LED signals, managing the communication protocol, calculating the flow, estimating the flow, calculating and adjusting the measurements according to calibration parameters, calculating compensation for temperature, viscosity, etc., performing linearization for non linear sensors, sending alarms, and general housekeeping tasks of the measuring device. The measuring device may optionally include a random access memory (RAM) (47) that may store the measurements so that they can be transmitted by the communication circuitry (78) at a later time, or may be retransmitted if the measuring device is connected to another receiving device than the one it was initially connected to, or upon request, or for some other reason. The optional RAM can also serve as the memory for the optional microprocessor/microcontroller/DSP (48). It can also serve as a memory for the optional flow estimation circuitry (49) if needed or for any other element in the measuring device that may require random access memory. The measuring device can include one or more optional RAM (47). The measuring device may optionally include one or more non volatile memory (NVM) and/or fuses or anti-fuses (46) for storing information like calibration data, measurements, device model number, device serial number, configuration data and/or any other information which may require a non volatile memory. The measuring device may optionally include one or more read only memory (ROM) or reprogrammable memory like FLASH memory (79) for storing the program code of the optional microprocessor/microcontroller/DSP (48) and/or for keeping linearization curves and/or the states of state machines and/or protocol information for the communication circuitry and/or for any other purpose that may require such memory.

Figure 8:
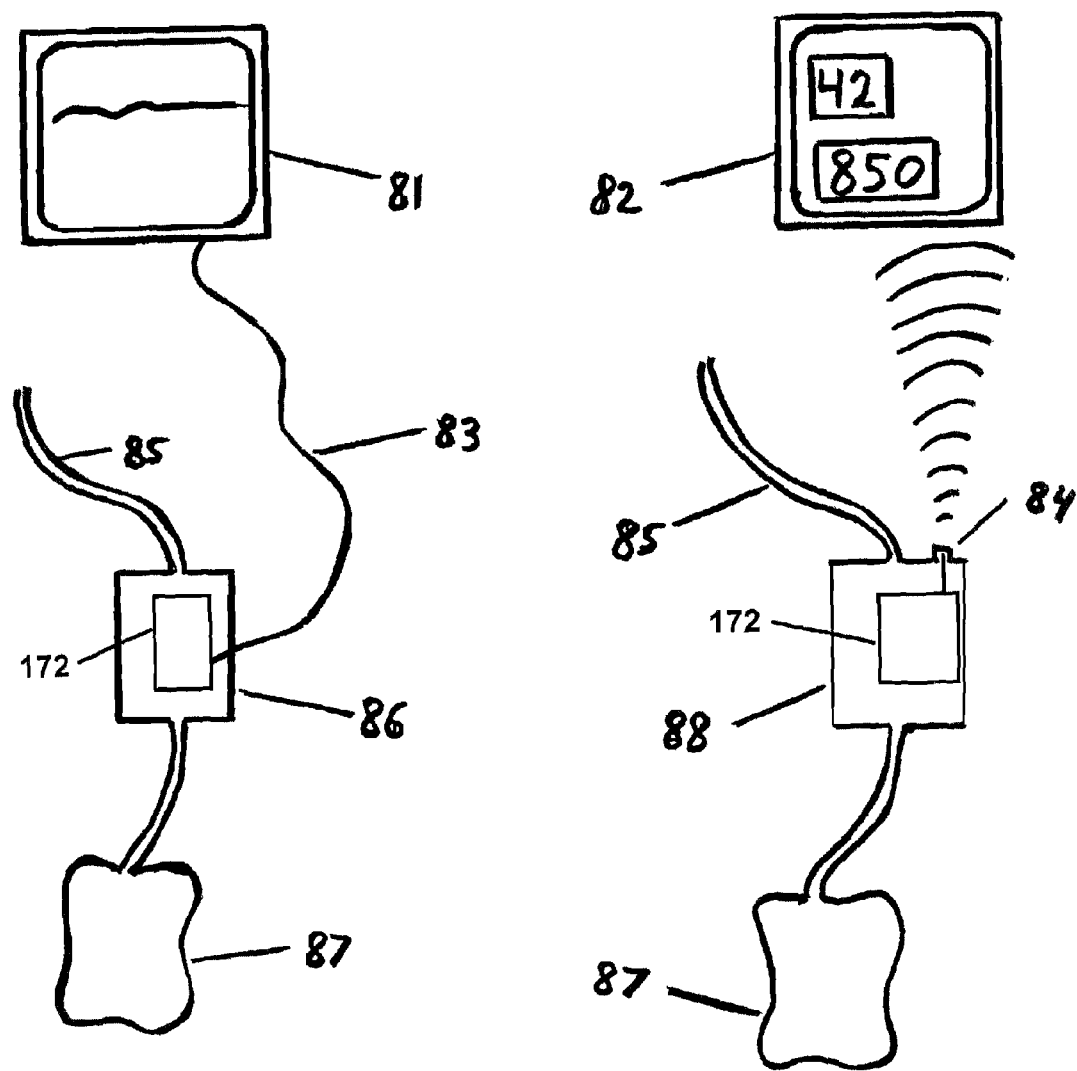
FIG. 8 shows the connection of the measuring device of the present invention to a dedicated monitor

Going to FIG. 8, two configurations for connecting the measuring device to a display unit according to some embodiments of the present invention are shown. On the figure of FIG. 8 displayed at the left side of the drawing sheet there may be a measuring device (86) that may receive urine from a tube (85) and may output it to a collecting bag (87). The measuring device may transmit the measurements to a display unit (81) through a wire (83). The measurements may be displayed graphically on the display. According to some embodiments of the present invention, the measuring device may transmit a signal indicative of excretion flow to an external device. According to some embodiments of the present invention, the signal may be transmitted through an electrical wire. The figure of FIG. 8 displayed on the right side of the drawing sheet shows a measuring device (88) that may receive urine from a tube (85) and may output it to a collecting bag (87). The measuring device may transmit the measurements to a display unit (82) through a wireless transmitter (84). According to some embodiments of the present invention, the measuring device may transmit a signal indicative of excretion flow to an external device wirelessly. The measurements may be displayed numerically on the display. In this example, the instantaneous flow rate of 42 ml/h and the amount of urine in the bag of 850 ml are displayed. Of course any other information that can be derived from measuring the urine flow can be displayed, as for instance, the amount of excretion during the last hour.

FIG. 9 shows a standard vital sign monitor (90) that may be connected to several probes like an arterial line (91) for measuring blood pressure, a pulse-oximeter (92) for measuring pulse rate and oxygen saturation in the blood, a urine measuring device (93) for measuring the urine excretion rate and volume, and ECG (94) for measuring cardio signals.

FIG. 10 shows a central monitor (99) in the nurses' station that may be connected to several urine measuring devices (95-98). The measuring devices may be connected to the monitor (99) either directly by a wired or wireless communication link or by an optical fiber, or through a communication network, or the measuring device can be connected to a receiving device that may take care of the transmission of the measurements to the monitor.

Figure 11:
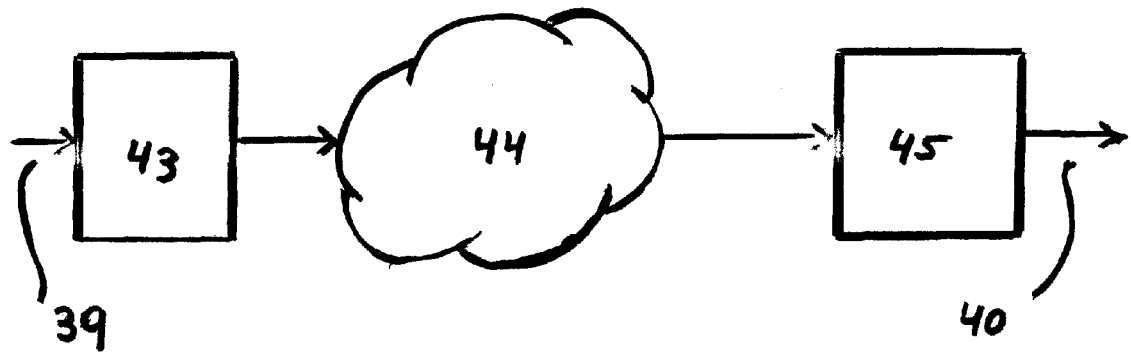
FIG. 11 shows a data communication setting

FIG. 11 describes a communication setting in which a transmitter (43) may receive a data stream from a communication link (39). The transmitter may encapsulate a fixed number of bits from the data stream received at the communication link (39) together with optional protocol headers and/or trailers into a packet. The transmitter may then transmit the information encapsulated in packets through a data communication network (44) to a receiver (45). The packets transmitted from the transmitter (43) may be transmitted at certain time intervals T in between each other as shown in FIG. 12. While the packets pass through the network (44), each packet may be delayed for a different amount of time before it reaches the receiver (45). When the packets reach the receiver, the time intervals between the packets may no longer be the same intervals as was when the packets were transmitted from the transmitter. FIG. 13 shows the packets as they may be received by the receiver with times T1, T2, T3, T4, . . . which can be equal to, or smaller or larger then T. Going back to FIG. 11, the receiver (45) may receive the packets from the communication network (44) and may strip off the header and/or trailer from the packets, and may transmit the data stream out to a communication link (40). The data stream going into the transmitter (43) from the communication link (39) may be at a certain rate which may cause packets to be transmitted from the transmitter to the network (44) at time intervals T. Since the packets may be received at the receiver (45) at time intervals other then T, the data stream sent to the communication link (40) may be at a rate which is different from the rate the data stream entered the transmitter (43) from communication link 39. In order to have the data stream coming out of communication link 40 be at the same rate as the data stream going into communication link 39, the time interval T in which the packets were transmitted by the transmitter (43) may need to be estimated by the receiver (45), this estimation can be done by using the time intervals between the received packets and applying certain algorithms which are beyond the scope of the present invention, on those time intervals.

Due to variations in physical conditions like temperature, the rate in which the data stream enters the transmitter (43) through the communication link (39) can vary, this may cause the time interval T in which the packets are transmitted by the transmitter (43) into the network (44) to vary. The estimation mechanism in the receiver (45) may need to be able to track the changes in the time interval T.

FIG. 14 shows the packets transmitted by the transmitter (36) with varying time intervals. The network may add jitter and wander to these time intervals in a way that the spacing in time between the packets may change (37). The receiver may receive the packets from the network and may estimate the original spacing between the packets (38) as it may have been transmitted by the transmitter (36).

FIG. 15 is another description of the result of the estimation mechanism. Packets may be transmitted by the transmitter (43) with time intervals T between the packets which may vary in the course of time (52). The network (44) may add jitter and wander to the time interval T (53). The receiver (45) may estimate the original time interval T' (54).

Figure 16:
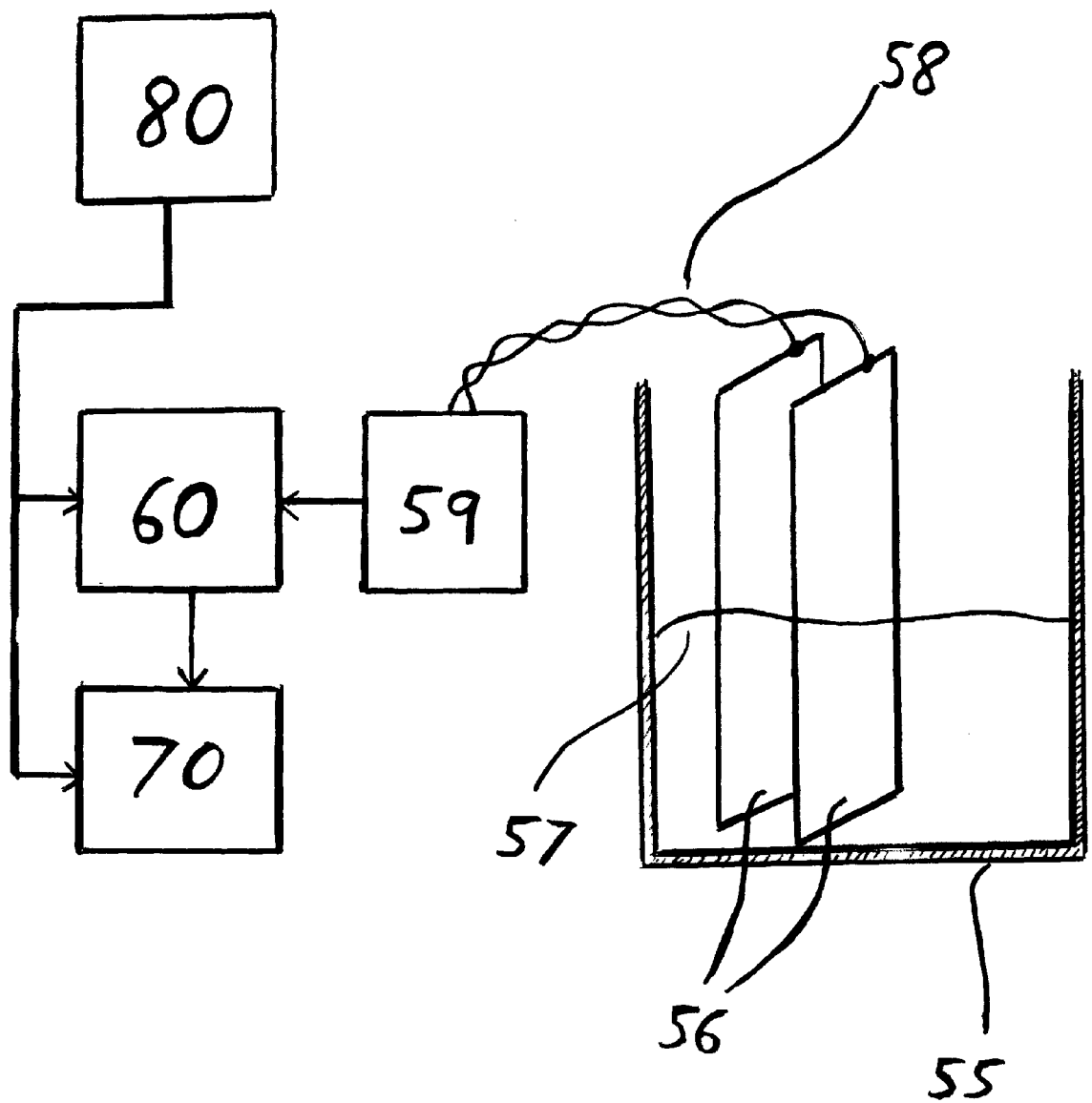
FIG. 16 shows an example of a capacitive, volume measuring device

FIG. 16 is an example of a way for measuring liquid flow by measuring the change of liquid quantity in a vessel (55) during a given period of time. The liquid quantity in the vessel (55) may be determined by measuring the height (57) of the liquid in the vessel. The vessel may have a two plate capacitor (56) placed in it vertically, the capacitor may be part of an oscillator circuit (59) and it may be connected to the oscillator circuit (59) with wires (58). The capacitance of the capacitor may be a function of the area of the plates, the distance between the plates, and the dielectric between the plates. When liquid accumulates in the vessel, it may also gradually fill in the gap between the plates and may change the dielectric between the two plates (56). The change in dielectric may change the capacitance of the capacitor. Since the capacitor may be part of an oscillator circuit (59), a change in the capacitance of the capacitor (56) may cause a similar or correlated change in the frequency of the oscillator, therefore, measuring the oscillator's frequency may indicate the liquid level (57) in the vessel. Multiplying the liquid level by (pi*r2) where 'pi' is 3.14 and 'r' is the vessel's radius may provide the quantity of the liquid. The oscillator (59) may be connected to a counter (60) which may count the number of oscillations of the oscillator. A timer (80) may latch the count of the counter (60) each second (or once in any other fixed amount of time) in a register (70) and at the same time may reset the counter (60). The captured number in the register (70) may be (or may be proportional to) the frequency of the oscillator (59). By subtracting the liquid quantity measured in the previous second (or other fixed amount of time) from the liquid quantity currently measured, the liquid flow may be determined.

Figure 17:
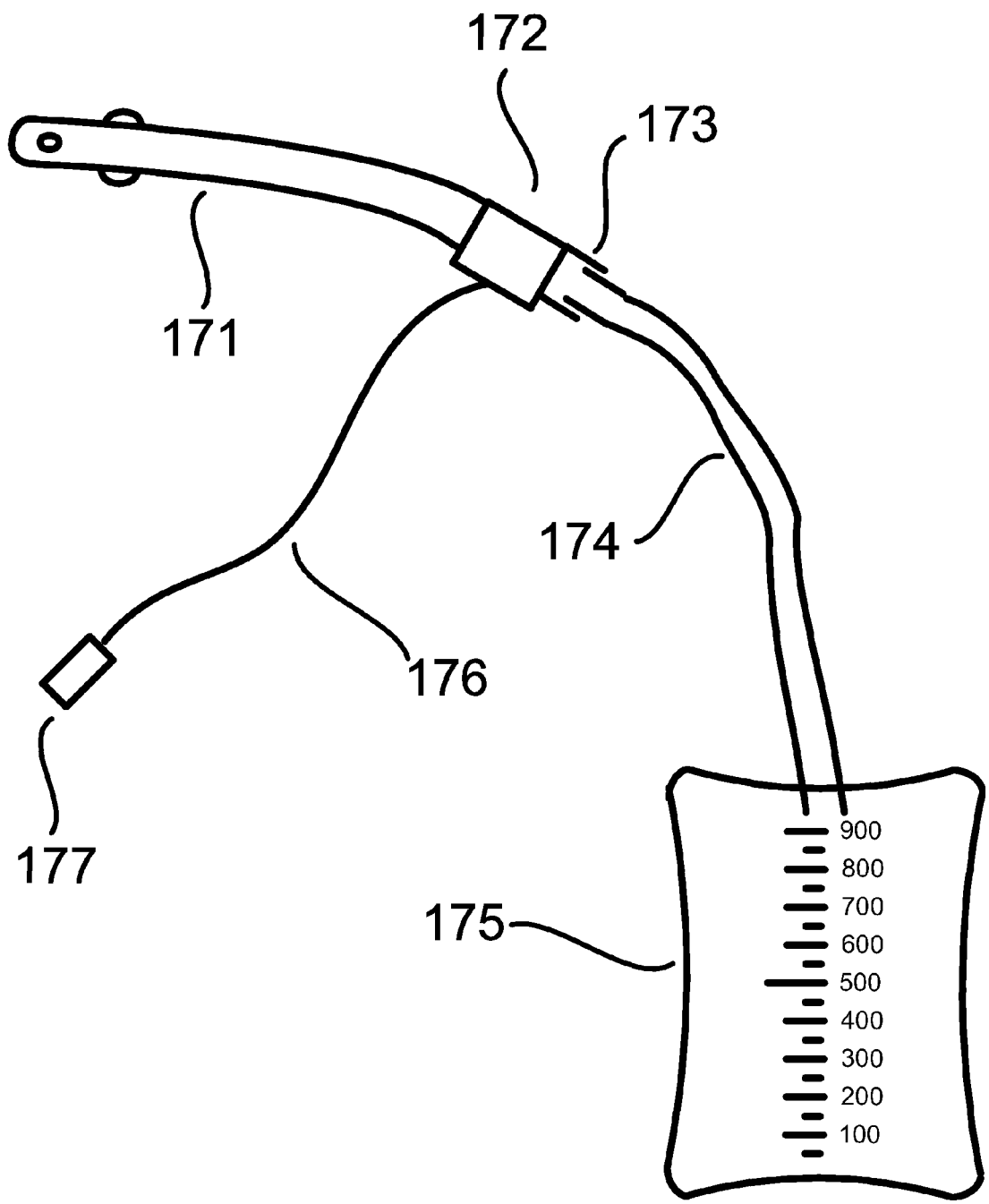
FIGS. 17 and 18 are examples of an excretion collection assembly according to the present invention

FIG. 17 shows an example of an excretion collection assembly according to some embodiments of the present invention. One end of a tube (174) may be connected to a catheter (171) through the catheter's connector (173), and the other end of the tube may be connected to a bag (175). A sensing module (172) or a portion of the sensing module may be integral with the catheter (171). The sensing module may transmit a signal indicative of the excretion flow and/or receive power through a wire (176). The wire (176) may include a connector (177) which may include a non volatile memory and/or other electrical components.

Figure 18:
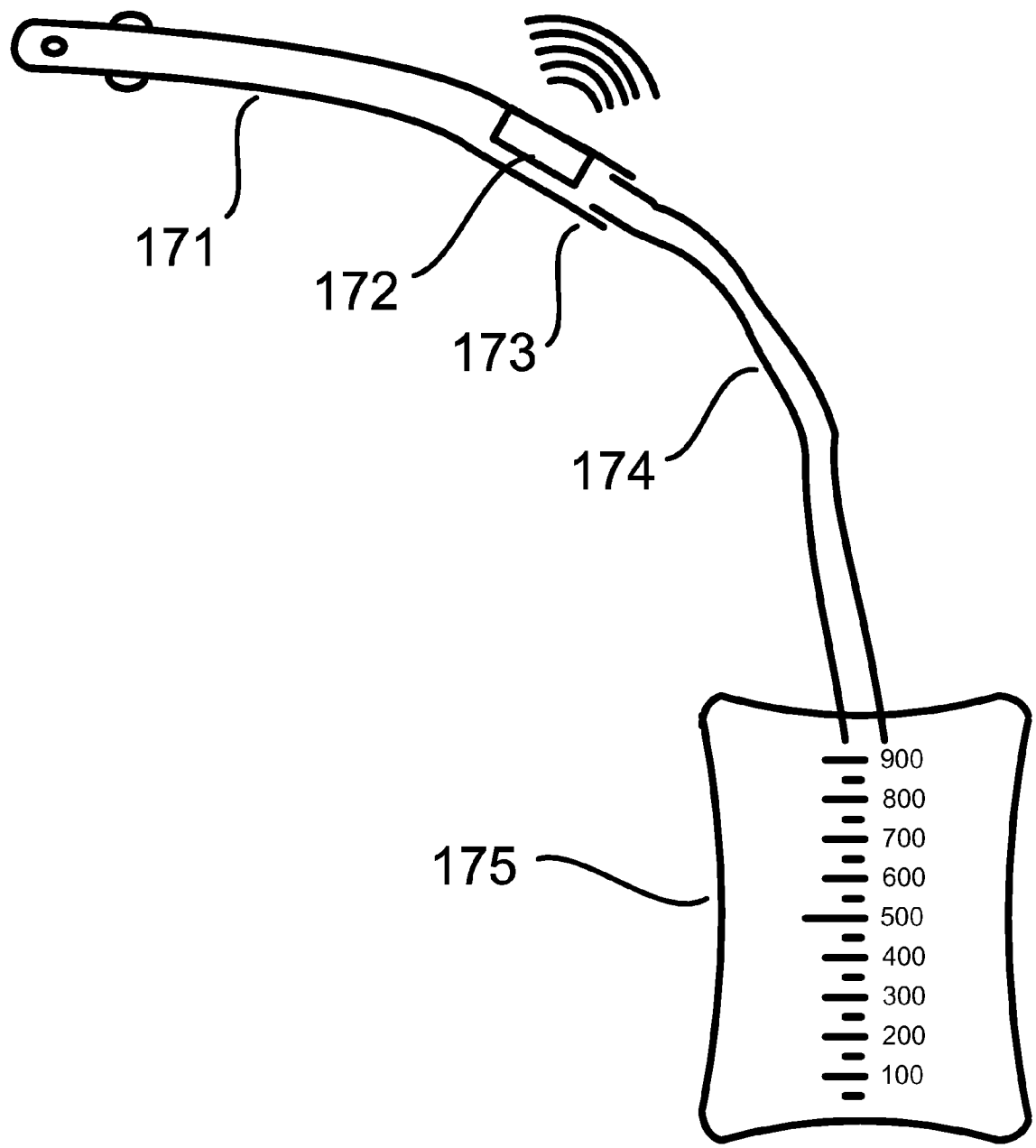

FIG. 18 shows another example of an excretion collection assembly according to some embodiments of the present invention. One end of a tube (174) may be connected to a catheter (171) through the catheter's connector (173), and the other end of the tube may be connected to a bag (175). A sensing module (172) or a portion of the sensing module may be integral with the catheter (171). The sensing module may transmit a signal indicative of the excretion flow wirelessly.

It will now be explained how the present invention may be implemented with the different embodiments, arrangements, and configurations. The different embodiments can be implemented with variations, modifications, alternatives, and alterations. These variations, modifications, alternatives, and alterations of the various embodiments, arrangements, and configurations may be used alone or in combination with one another as will become more readily apparent to those with skill in the art.

Measuring a low rate flow of body liquids like urine or blood, wherein the measuring device (sensing module) may have to keep a high level of sterility while being very accurate and with very fine resolution, as well as being able to operate in the tough conditions of operating rooms and ICUs may require a very innovative design of the measuring device.

FIG. 3 shows an example of an excretion collection assembly that may include a catheter (32), a tube (24), a measuring device or measurement probe (28), and a bag (34).

According to some preferred embodiments of the present invention, there may be a system for determining a flow rate of an excretion stream within an excretion collection assembly, that may include a sensing module at least a portion of which is integral with a constituent element of the collection assembly, wherein said sensing module may include at least one electrical component and/or at least one electromechanical component.

According to some embodiments of the present invention, the excretion collection assembly may include a catheter, a tube, and a bag.

According to some embodiments of the present invention, at least a portion of the sensing module may be integral with a tube of the assembly.

According to some embodiments of the present invention, at least a portion of the sensing module may be integral with a bag of the assembly.

According to some embodiments of the present invention, at least a portion of the sensing module may be integral with a catheter of the assembly.

According to some embodiments of the present invention, the excretion collection assembly may include a catheter, a measurement probe, a tube, and a bag.

According to some embodiments of the present invention, at least a portion of the sensing module may be integral with a measurement probe of the assembly.

In another embodiment of the present invention there may be a system for determining a flow rate of a liquid stream that may include at least one electrical and/or electromechanical component housed together with the medium through which the liquid flows.

In another embodiment of the present invention there may be a system for determining a flow rate of a liquid stream that may include at least one electrical and/or electromechanical component housed together with the sterile medium through which the liquid flows. In another embodiment of the present invention there may be a system for determining a flow rate of a liquid stream that may include at least one electrical and/or electromechanical component housed together with the medium through which the liquid flows, and which can be sterilized. In another embodiment of the present invention there may be a system for determining a flow rate of a liquid stream that may include at least one electrical and/or electromechanical component housed together with the medium through which the liquid flows, and which said system is sterilized. In another embodiment of the present invention there may be a system for determining a flow rate of a liquid stream that may include at least one electrical and/or electromechanical component housed together with the medium through which the liquid flows constructed in a way and from components so that it can be sterilized.

The flow measurement can be done in one of many ways already known in the art or that are yet to be invented. In whatever technique is used for measuring the flow, the flow may be sensed by some sensing element which may be part of a circuitry that may determine the flow. As an example, consider a capacitive technique that may determine the liquid level in a vessel according to the change in capacitance of a capacitor that may be immersed in the vessel (FIG. 16). In this case the capacitor (56) can be part of an oscillator circuit (59), the frequency in which the oscillator circuit may oscillate may depend on the capacitor's capacitance. The circuit can then include a counter (60) that may count the number of oscillations in a given amount of time, and that count can be latched in a register (70) after each such amount of time elapsed. The latched count may be proportional to the frequency which may be proportional to the capacitor's capacitance, which in turn may be proportional to the liquid level (57) in the vessel. In another embodiment of the present invention the at least one electrical and/or electromechanical component of the system for determining a flow rate of a liquid stream may include at least one sensing element for sensing the flow, housed together with the medium through which the liquid flows. The sensing element can be an electrical component as in the capacitive technique just mentioned, or it can be a mechanical element combined with an electrical component as in, for example, the variable area type of devices. In another embodiment of the present invention there may be a system for determining a flow rate of a liquid stream that may include at least one electrical and/or electromechanical component housed together with the medium through which the liquid flows and housed together with the flow sensing element.

In some implementations of liquid flow measurement, the measuring device may need to be calibrated. Let's look at the example used above of a capacitive sensor. In this example, there can be many variances in the elements that determine the flow, for instance, in the capacitor's capacitance, in the electronic circuitry component values, in the vessel's diameter, etc. All these variations may need to be compensated for when determining the flow of the measured liquid. During, or after manufacturing, a calibration step may take place in which calibration information may be extracted, this calibration information may be used for compensating for the variations in the different components' values. According to some embodiments of the present invention, the system for determining a flow rate of an excretion stream may include a calibration parameter. According to some embodiments of the present invention, the calibration parameter may reflect at least one characteristic of the electrical circuit and/or electromechanical circuit. According to some embodiments of the present invention, the calibration parameter may be adjusted during production or sorting of the electrical circuit and/or electromechanical circuit. According to some embodiments of the present invention, the calibration parameter may reflect at least one characteristic of the electrical component and/or electromechanical component. According to some embodiments of the present invention, the calibration parameter may be adjusted during production or sorting of the electrical component and/or electromechanical component. According to some embodiments of the present invention, the calibration parameter may be adjusted during production or sorting of the sensing module. According to some embodiments of the present invention, the calibration parameter may be adjusted during production or sorting of the measurement probe. According to some embodiments of the present invention, the sensing module may include a non volatile memory (NVM). In another embodiment of the present invention the at least one electrical and/or electromechanical component of the measuring device may include at least one non volatile memory (NVM). This non volatile memory can be used among other things like for storing the device model or serial number, also for storing the calibration data. It should be noted that the calibration data can be stored in the measuring device whether the sensing element and/or the sensing circuitry is part of the measuring device or not.

In cases where the patient may be moved from one location to another, like from the ICU to an x-ray room and back, and in which during that time the measuring device may be disconnected from the receiving device or displaying device, it may be required that the urine excretion will still be logged during that time. In another embodiment of the present invention the at least one electronic circuit of the measuring device may include at least one random access memory (RAM) for storing measurements. According to some embodiments of the present invention, the sensing module may include a random access memory (RAM). In some embodiments of the present invention, the same memory or memories may be used for other purposes as for instance, the memory for a calculating logic that may calculate the flow, or as the memory of a microprocessor that might be in the measuring device. In yet another embodiment of the present invention, the measurements can be logged in a non volatile memory (NVM). In this embodiment, the NVM can be the same one as for storing other information such as calibration data, or it can be a separate one.

The measured flow can be read in one of, or several possible ways. In one embodiment of the present invention, the measured flow can appear as a voltage on an electrical port on the measuring device, for instance, 0 volts may determine that there is no flow and 5 volts may determine the maximum flow in the measuring device's measuring range, and voltages in between 0 to 5 volts may represent flows in between 0 to maximum flow. In another embodiment of the present invention, the measured flow can appear as pulses on an electrical port on the measuring device in such a way that each pulse may represent an amount of liquid that flowed through the measuring device, for instance, each pulse may represent 10 micro liters. In another embodiment of the present invention, the measured flow can appear as short circuit pulses or open circuit pulses on an electrical port on the measuring device in such a way that each short circuit or open circuit pulse may represent an amount of liquid that flowed through the measuring device, for instance, each pulse may represent 10 micro liters. In another embodiment of the present invention, the measured flow can appear as a square wave on an electrical port on the measuring device in such a way that the duty cycle of each cycle may represent an amount of liquid that flowed through the measuring device, for instance, 0% duty cycle may determine that there is no flow and 100% duty cycle may determine the maximum flow in the measuring device's measuring range, and duty cycles in between 0% to 100% may represent flows in between 0 to maximum flow. In another embodiment of the present invention, the at least one electronic circuit of the measuring device may include at least one communication circuit that may transmit the measured information to a receiving device or to any number of receiving devices. The information can be transmitted in any agreed upon way between the measuring device and the receiving device, for instance, in packets, in cells, or some other way. It may be transmitted in a proprietary protocol or in some standard protocol, in a local area network (LAN) connection or wide area network (WAN) or some other way like a short haul modem or long haul modem or a direct connection, in any physical layer like RS-232 or RS-485 or V.35, 10 BaseT, 100 BaseT, 802.11 or single mode fiber or multimode fiber or IrDA or Bluetooth or any other standard or non standard way. In any asynchronous or synchronous way. In any encoding like NRZ, RZ, CDP, Manchester, 4B/5B, 8B/10B or any other way. The measurement can also be transmitted from the measuring device in protocols like TCP/IP, UDP and others. The measurement can be transmitted in a standard OSI Model way or otherwise in some proprietary way. According to some embodiments of the present invention, the electrical component and/or electromechanical component within the sensing module may be adapted to transmit a signal indicative of excretion flow to an external device. According to some embodiments of the present invention, the electrical component and/or electromechanical component within the sensing module may be adapted to transmit a signal indicative of excretion flow to an external device through an electrical wire. According to some embodiments of the present invention, the electrical wire may include a connector which may include a non-volatile memory. According to some embodiments of the present invention, the electrical component and/or electromechanical component within the sensing module may be adapted to transmit a signal indicative of excretion flow to an external device wirelessly.

In another embodiment of the present invention there may be a system for determining and transmitting a flow rate of a liquid stream that may include at least one electronic circuit housed together with the medium through which the liquid flows.

The measured values according to the present invention can be transmitted to a receiving device which may display them or may transfer them to another device or monitor for display. In another embodiment of the present invention, there may be a system for determining a flow rate of a liquid stream which may not include means for displaying the measured values. In another embodiment of the present invention, there may be a system for determining a flow rate of a liquid stream which may not include means for displaying the measured values, and may include at least one electronic circuit housed together with the medium through which the liquid flows.

The urine flow of interest may be the urine flowing into the bladder. The urine flowing into the measuring device may pass through several physical elements like the bladder and tubes, which may distort the flow rate in a way that the long time average of the amount of urine flowing into the bladder may be close to the amount of urine coming out of the bladder, but the instantaneous flow may differ. The elements that may distort the flow may include the bladder, the Foley catheter, the tubing and/or the measuring device itself. In order to present the flow of interest (the flow into the bladder), it may need to be estimated from the measured flow in the measuring device. The flow can be estimated by well known algorithms such as those that can be adopted from the communication world. This estimation can be done in the measuring device or in the receiving device or elsewhere. In one embodiment of the present invention, these algorithms may be implemented in a CPU or a DSP or a microcontroller, the CPU or DSP or microcontroller can serve for other tasks as well, for instance for controlling the measuring device. In another embodiment of the present invention, these algorithms may be implemented in a dedicated circuitry that may perform the flow estimation algorithm.

The measuring device may require some circuitry for its operation. The circuits may include sensor circuitry, flow estimation circuitry, general control circuitry as for lighting LED signals, communication circuitry for sending the measurements to the receiving device, flow calculation circuitry that may calculate the flow rate according to the sensor measurements and can compensate for temperature and calibration errors, etc. In one embodiment of the present invention, the circuitry of the measuring device may be implemented with random logic and/or analog circuitry, this can be very efficient in terms of cost and power consumption.

In another embodiment of the present invention, the at least one electronic circuit of the measuring device may include at least one transistor.

In another embodiment of the present invention, part of the circuitry functionality may be done with a microprocessor or a DSP that may be included in the measuring device, this may have the advantage of flexibility. In yet another embodiment of the present invention, part of the circuitry functionality may be done with a microcontroller that may be included in the measuring device which may also have the advantage of flexibility and typically may cost less than a microprocessor or a DSP and may consume less power.

In another embodiment of the present invention, the at least one electronic circuit of the measuring device may include at least one FLASH memory that among other things can serve as the program memory for a microprocessor or microcontroller or DSP, it can store tables which can be used by a processor or the random logic like linearization tables, it can store the states of state machines, etc.

In order to save costs and reduce power consumption as well as minimize the size of the measuring device and make it less sensitive to noise like RFI. In some embodiments of the present invention part or all of the electronic circuitry may be integrated into a single integrated circuit (IC) or it may be divided among several integrated circuits. According to some embodiments of the present invention, the electrical component of the system for determining a flow rate of an excretion stream may be an integrated circuit (IC).

In order to prevent bacteria from entering the measuring device and getting into the patient's bladder, the measuring device may need to be sterilized. In some embodiments of the present invention, the measuring device may be fully disposable and may not be transferred from one patient to another. In other embodiments of the present invention, the measuring device can be cleaned and sterilized for reuse.

One of the applications of the system of the present invention may be to measure urine excretion flow rate and volume. In some embodiments of the present invention, the measuring device may be directly or indirectly connected to a urinary catheter at the liquid flow input of the measuring device. In some embodiments of the present invention, the measuring device may be directly or indirectly connected to a urine drainage bag or container at the liquid flow output of the measuring device. In other embodiments of the present invention, the measuring device may be an integral part of the urine drainage bag or container. In other embodiments of the present invention, the measuring device may be an integral part of the urinary catheter.

The measuring device may continuously or periodically or upon request or on any change in flow, transmit the measurements to a device or to several devices that may receive the measurements and can further process it and/or display it and/or log it and/or initiate an alarm and/or transmit it to other devices and/or control other devices and/or perform any other action based on the measurements. In some embodiments of the present invention, the measurement may be transmitted over at least one communication link to at least one receiving device.

The measuring device can be powered from a single power source or from several power sources. Powering the measuring device from several power sources can be done for several reasons, one reason might be for backup, another reason might be that one power source may be a main power source which may charge a small rechargeable power source for periods when the main power source may be disconnected as when moving the patient from one room to another. According to some embodiments of the present invention, the electrical component and/or electromechanical component of the system for determining a flow rate of an excretion stream may be powered by at least one battery. According to some embodiments of the present invention, the electrical component and/or electromechanical component of the system for determining a flow rate of an excretion stream may be powered by at least one rechargeable battery. According to some embodiments of the present invention, the electrical component and/or electromechanical component of the system for determining a flow rate of an excretion stream may be powered by a chemical reaction associated with the excretion. According to some embodiments of the present invention, the electrical component and/or electromechanical component of the system for determining a flow rate of an excretion stream may receive power through an electrical wire that may be connected to an electrical power source. In some embodiments of the present invention, the measuring device may be powered by at least a battery. In some embodiments of the present invention, at least one battery may be disposable. In other embodiments of the present invention, at least one battery may be rechargeable. In other embodiments of the present invention, the measuring device may be powered by at least a chemical reaction with a biofluid as for instance by placing magnesium and copper probes in contact with the biofluid. In some embodiments of the present invention, the biofluid may be urine. In other embodiments of the present invention, the biofluid may be blood. In other embodiments of the present invention, the biofluid may be an intravenous solution. In some embodiments of the present invention, the measuring device may be powered by at least a wire that may be connected to it from a power source. In some embodiments of the present invention, the power source may be part of, or housed together with, or located next to the receiving device. In other embodiments of the present invention, the measuring device may be powered by at least a magnetic field. In other embodiments of the present invention, the measuring device may be powered at least by energy of light. In some embodiments of the present invention, the light may be transferred from a light or laser source through at least one optical fiber. In other embodiments of the present invention, the light or laser source may be part of, or housed together with, or located next to the receiving device.

The measurements can be transmitted to the receiving device or devices over any number of communication links of the same or different kinds. In some embodiments of the present invention, at least one communication link may be at least one radio link. In other embodiments of the present invention, at least one communication link may be at least one infra-red link. In other embodiments of the present invention, at least one communication link may be at least one electrical cord. In other embodiments of the present invention, at least one communication link may be at least one power wire. In other embodiments of the present invention, at least one communication link may be at least one fiber-optic link. In other embodiments of the present invention, at least one optical fiber may also be used for the power light.

In order to be able to meet requirements of simplicity, mobility—for being able to transfer the patient from one location to another without disrupting the measurement, immunity to chemicals and water showers, immunity to mechanical hits, ease of use, no alignment problems, and no wearing out. In some embodiments of the present invention, the measuring device may not be physically and mechanically connected to any other device that may include any of:
a) electronic circuitry
b) active mechanical element like valves, stirs, pumps, motors, etc.
c) passive mechanical elements like transducers, strain-gages, propellers, etc.
d) electronic element like LEDs, photodiodes, phototransistors, lasers, resistors, capacitors, inductors, transistors, etc.

According to some embodiments of the present invention, there may be a system for determining a flow rate of an excretion stream which may be discrete. According to these embodiments, discrete may mean that the system may not need to be mechanically attached to any other device, the system may be connected to other devices by an electrical wire and/or by an optical fiber and/or wirelessly.

In many implementations of a measuring device there may be differences between the measurements of one device to another device of the same kind. These differences may be due to variations in value or size of different components that the measuring device is made of. One cause can be a difference in the physical size of the mechanical elements included in the measuring device. For example, a measuring device that uses a vessel for collecting the liquid may have a volume of (pi*r2*h) where 'pi' is 3.14 . . . , 'r' is the vessel's radius, and 'h' is the vessel's height. As an example let's assume a nominal radius of 10 mm and a manufacturing variation of 1 mm, in this case the error in volume may be (102−92)/102 which is a 19% error. Another cause can be variations in the actual value of the electrical components that participate in the sensing circuit. Another cause can be alignment accuracy of the manufacturing process. Each of these as well as other factors may contribute to the inaccuracy of the measurement. In order to have accurate measurements, the measuring device can be calibrated and calibration information can be stored in the measuring device. In some embodiments of the present invention, the measuring device may include means for storing calibration data. In some embodiments of the present invention, the calibration data may be stored at least, in at least one non volatile memory. In other embodiments of the present invention, the calibration data may be stored by burning fuses or anti-fuses. In other embodiments of the present invention, the calibration data may be laser trimmed. In other embodiments of the present invention, the calibration may be mechanically adjusted.

The measuring device may be able to operate independently and may not need to be connected to a display or a receiving device while measuring the flow of a liquid that flows through it. Once in a while or at request, the measuring device can be connected via a communication link, which can be wired or wireless, to a receiving device or a display for displaying and/or storing and/or transmitting the measurements. There may be a need to display the history of excretion also in cases when the measuring device is connected to a receiving device or a display but the patient may be moved to another room for some reason, like for doing x-ray or an operation, and the measuring device may be disconnected from the display and may be reconnected to another display in the other location. For these reasons and others there may be a need to log the measurements in the measuring device. In some embodiments of the present invention, the measuring device may include at least one memory for storing the measurements.

In some applications in which the measuring device may be used, urine excretion flow rate may be measured. In order to measure the urine excretion flow, a catheter may be inserted through the urethra and into the patient's bladder. The other end of the catheter may be connected to the measuring device which may measure the flow rate of the urine flowing through it. In some embodiments of the present invention, the measuring device may be connected to the catheter with at least one tube. In order to prevent air from entering the tube or tubes connecting the catheter to the measuring device, in some embodiments of the present invention, the tube or tubes may be of a diameter of less than 8 mm. In other embodiments of the present invention, the tube or tubes may be of a varying diameter as depicted as an example in (FIGS. 6a and 6b). In yet some other embodiments of the present invention, at least one point of the at least one tube may have a diameter of less than 8 mm. In other embodiments of the present invention, the at least one tube may be connected to at least one outlet which may be of a diameter of less than 8 mm (FIG. 5). In other embodiments of the present invention, the at least one tube may be an integral part of the measuring device. Since the tube that may connect the catheter and the measuring device may have a volume which may need to fill up before the measured liquid reaches the measuring device, the measuring device may not measure any liquid flow until that volume may be filled. For example, using a tube which has a volume of 100 ml for measuring urine flow at a rate of 50 ml/hour may take two hours until the tube is filled and the measuring can start. In order to prevent this "dead" time, in some embodiments of the present invention, the at least one tube may initially be filled with liquid which may not necessarily be the same material as the measured liquid, in this way, any amount of liquid that may enter the tube or tubes at the inlet, may cause the exact same amount of liquid to come out of the outlet of the tube or tubes and be measured. In some embodiments of the present invention, the liquid in the tube or tubes may be filled by a hospital staff. In other embodiments of the present invention, the liquid in the tube or tubes may be filled before it gets to the hospital. In other embodiments of the present invention, the liquid in the tube or tubes may be filled in the factory.

On many occasions, the flow of interest may be at one point while the measurement may be done at another point along the liquid stream, while in between the two points there can be medium that may affect the instantaneous flow rate. In these cases there may be a need to estimate the flow rate at the point of interest from the measurements that may be done at the point of measure. This estimation can be done in various ways like computation using a microprocessor or microcontroller or DSP, or computation using dedicated hardware or by implementing a digital or analog filter. In some embodiments of the present invention, the flow at a certain location may be estimated from the measured flow at another location.

According to some embodiments of the present invention, there may be a system for determining a flow rate of an excretion stream within an excretion collection assembly which may include a sensing module at least a portion of which may be integral with a constituent element of the collection assembly, wherein the sensing module may include a passive electrical element such as coil, piezoelectric crystal, motor, solenoid, capacitor, resistor, light emitting diode (LED), laser diode, thermocouple, bimetal and switch. In some embodiments of the present invention, the system may be powered by at least a chemical reaction with urine. In some embodiments of the present invention, the measured liquid may be urine. In other embodiments of the present invention, the system may be powered by at least a chemical reaction with blood. In other embodiments of the present invention, the measured liquid may be blood. In other embodiments of the present invention, the system may be powered by at least a chemical reaction with an intravenous solution. In other embodiments of the present invention, the measured liquid may be an intravenous solution.

In some embodiments of the present invention, there may be a method of connecting an electronic urine measuring device to a patient that may include the step of connecting the inlet of the measuring device to a urinary catheter.

In some embodiments of the present invention, there may be a method of connecting an electronic urine measuring device to a patient that may include the steps of:
a) connecting the inlet of the measuring device to a tube
b) connecting the tube to a urinary catheter.

In some embodiments of the present invention, there may be a method of connecting an electronic urine measuring device that may have a tube at its inlet to a patient and that may include the step of connecting the tube to a urinary catheter.

In some embodiments of the present invention, there may be a method that may include a step of filling the tube with liquid.

In some embodiments of the present invention, there may be a method that may include a step of connecting the measuring device to a receiving device.

In some embodiments of the present invention, there may be a method that may include a step of connecting the measuring device to power.

It should be understood that all of the features and all of the objectives described in the specification are exemplary, any one of which may be altered or completely removed without detracting from the breadth of the present invention, which breadth can only be determined in view of claims yet to be allowed.

The invention claimed is:

1. A system for estimating a rate of urine produced by kidneys and flowing into a bladder based on measurement of an excretion stream within an excretion collection assembly including a catheter, said system comprising:
    a urinary catheter, of the excretion collection assembly, configured to be inserted into a bladder such that urine entering the bladder exits through said catheter and flows through at least part of the excretion collection assembly;
    a measuring device at least a portion of which is integral with a constituent element of the excretion collection assembly, wherein said measuring device comprises:
        a sensing element for sensing a rate of urine flow out of the bladder;
        first circuitry connected to the sensing element to produce a signal indicative of the rate of urine flow out of the bladder, wherein said electronic circuitry includes at least one analog or at least one digital component functionally associated with said sensing element; and second circuitry to estimate a present urine flow into the bladder based on the flow indicative signal produced by said first circuitry.

2. The system according to claim 1, wherein at least a portion of said device is integral with a tube of the assembly.

3. The system according to claim 1, wherein at least a portion of said device is integral with a bag of the assembly.

4. The system according to claim 1, wherein at least a portion of said device is integral with a catheter of the assembly.

5. The system according to claim 1, wherein at least a portion of said device is integral with a measurement probe of the assembly.

6. The system according to claim 1, wherein said device includes a non volatile memory (NVM).

7. The system according to claim 1, wherein said device includes a random access memory (RAM).

8. The system according to claim 1, wherein said first or second circuitry are an integrated circuit (IC).

9. The system according to claim 1, wherein said first or second circuitry are powered by at least one battery.

10. The system according to claim 9, wherein the battery is a rechargeable battery.

11. The system according to claim 1, wherein said first or second circuitry or said sensing element are powered by a chemical reaction associated with the excretion.

12. The system according to claim 1, wherein said first or second circuitry receive power through an electrical wire connected to an electrical power source.

13. The system according to claim 1, wherein said first or second circuitry are adapted to transmit a signal indicative of excretion flow to an external device.

14. The system according to claim 13, wherein said first or second circuitry are adapted to transmit the signal through an electrical wire.

15. The system according to claim 14, wherein said wire includes a connector including a non-volatile memory.

16. The system according to claim 13, wherein said first or second circuitry are adapted to transmit the signal wirelessly.

17. The system according to claim 1, wherein said system is discrete.

18. The system according to claim 1, wherein said system utilizes a calibration parameter.

19. The system according to claim 18, wherein said calibration parameter reflects at least one characteristic of said first or second circuitry or said sensing element.

20. The system according to claim 18, wherein said calibration parameter is adjusted during production or sorting of said first or second circuitry or said sensing element.

* * * * *